US012629500B2

(12) United States Patent
Lindekugel et al.

(10) Patent No.: US 12,629,500 B2
(45) Date of Patent: May 19, 2026

(54) SPLITTABLE NEEDLE FOR CATHETER PLACEMENT SYSTEM

(71) Applicant: Bard Access Systems, Inc., Salt Lake City, UT (US)

(72) Inventors: Eric W. Lindekugel, Salt Lake City, UT (US); Daniel B. Blanchard, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 670 days.

(21) Appl. No.: 17/989,325

(22) Filed: Nov. 17, 2022

(65) Prior Publication Data

US 2023/0149667 A1     May 18, 2023

Related U.S. Application Data

(60) Provisional application No. 63/281,008, filed on Nov. 18, 2021.

(51) Int. Cl.
A61M 25/06          (2006.01)
A61M 25/09          (2006.01)

(52) U.S. Cl.
CPC .... A61M 25/0668 (2013.01); A61M 25/0631 (2013.01); A61M 25/09 (2013.01)

(58) Field of Classification Search
CPC ...... A61M 25/0668; A61M 2025/0675; A61M 25/0631
See application file for complete search history.

(56) References Cited

U.S. PATENT DOCUMENTS

| | | | |
|---|---|---|---|
| 3,076,457 A | 2/1963 | Copen | |
| 3,359,978 A | 12/1967 | Smith, Jr. | |

(Continued)

FOREIGN PATENT DOCUMENTS

| | | |
|---|---|---|
| CN | 106422031 B | 7/2021 |
| CN | 114870208 A | 8/2022 |

(Continued)

OTHER PUBLICATIONS

Adam et al. (Gastrointestinal Endoscopy vol. 77, No. 5S 2013, 1020) (Year: 2010).

(Continued)

*Primary Examiner* — William R Carpenter
(74) *Attorney, Agent, or Firm* — Rutan & Tucker LLP

(57)          ABSTRACT

Advanced catheter placement systems require disengaging a needle from the guidewire without disturbing a position of the guidewire within the vasculature. Embodiments include withdrawing the needle proximally and drawing the needle over a splitter system that includes a splitter wedge. The splitter system separates the needle along a longitudinal axis. A portion of the guidewire can then pass between a first portion and a second portion of the needle, allowing the needle to disengage the guidewire. A catheter disposed on a proximal portion of the guidewire can then be advanced thereover into the vasculature. A needle safety system can adhere a puncture-resistant adhesive tape to the split portions of the needle. The tape can encapsulate the portions of the needle mitigating any damage or trauma caused by sharpened edges of the needle portions.

28 Claims, 21 Drawing Sheets

(56) References Cited

U.S. PATENT DOCUMENTS

| | | | |
|---|---|---|---|
| 3,539,034 A | | 11/1970 | Tafeen |
| 4,411,654 A | * | 10/1983 | Boarini ............. A61M 25/0668 |
| | | | 604/161 |
| 4,743,265 A | | 5/1988 | Whitehouse et al. |
| 4,886,507 A | | 12/1989 | Patton et al. |
| 4,935,008 A | | 6/1990 | Lewis, Jr. |
| 4,957,489 A | * | 9/1990 | Cameron .......... A61M 25/0637 |
| | | | 604/161 |
| 4,988,356 A | | 1/1991 | Crittenden et al. |
| 4,994,040 A | | 2/1991 | Cameron et al. |
| 5,255,690 A | | 10/1993 | Keith et al. |
| 5,261,887 A | | 11/1993 | Walker |
| 5,290,244 A | | 3/1994 | Moonka |
| 5,380,290 A | | 1/1995 | Makower et al. |
| 5,687,727 A | * | 11/1997 | Kraus ............... A61M 25/0169 |
| | | | 604/161 |
| 5,735,813 A | | 4/1998 | Lewis |
| 5,836,306 A | | 11/1998 | Duane et al. |
| 5,853,391 A | | 12/1998 | Bell |
| 5,971,957 A | | 10/1999 | Luther et al. |
| 6,019,736 A | | 2/2000 | Avellanet et al. |
| 6,159,195 A | | 12/2000 | Ha et al. |
| 7,172,587 B2 | | 2/2007 | Poole et al. |
| 7,938,820 B2 | | 5/2011 | Webster et al. |
| 8,882,713 B1 | | 11/2014 | Call et al. |
| 2002/0004635 A1 | | 1/2002 | Yock |
| 2002/0072712 A1 | | 6/2002 | Nool et al. |
| 2003/0205843 A1 | | 11/2003 | Adams |
| 2004/0092879 A1 | | 5/2004 | Kraus et al. |
| 2004/0236346 A1 | | 11/2004 | Parker |
| 2005/0021124 A1 | | 1/2005 | Cunniffe et al. |
| 2005/0043684 A1 | | 2/2005 | Basta et al. |
| 2005/0251092 A1 | | 11/2005 | Howell et al. |
| 2006/0129091 A1 | | 6/2006 | Bonnette et al. |
| 2007/0100294 A1 | | 5/2007 | Sugita et al. |
| 2007/0276288 A1 | | 11/2007 | Khaw |
| 2008/0009793 A1 | | 1/2008 | Dabbs |
| 2008/0027380 A1 | | 1/2008 | Wholey et al. |
| 2008/0091137 A1 | | 4/2008 | Reavill |
| 2008/0262430 A1 | | 10/2008 | Anderson et al. |
| 2009/0187147 A1 | | 7/2009 | Kurth et al. |
| 2011/0071502 A1 | | 3/2011 | Asai |
| 2013/0184659 A1 | | 7/2013 | Byrnes et al. |
| 2014/0100552 A1 | | 4/2014 | Gallacher et al. |
| 2015/0119806 A1 | | 4/2015 | Blanchard et al. |
| 2015/0224287 A1 | | 8/2015 | Bian et al. |
| 2015/0314109 A1 | | 11/2015 | Minar et al. |
| 2015/0320968 A1 | | 11/2015 | Konstantino et al. |
| 2016/0175563 A1 | | 6/2016 | Woehr et al. |
| 2016/0220786 A1 | | 8/2016 | Mitchell et al. |
| 2016/0310704 A1 | | 10/2016 | Ng et al. |
| 2017/0035996 A1 | | 2/2017 | O'Fallon |
| 2017/0258489 A1 | | 9/2017 | Galili et al. |
| 2017/0296792 A1 | | 10/2017 | Ornelas Vargas et al. |
| 2018/0043138 A1 | | 2/2018 | Chu |
| 2019/0015637 A1 | | 1/2019 | Jacobs |
| 2019/0022353 A1 | | 1/2019 | Khanicheh et al. |
| 2019/0022359 A1 | | 1/2019 | Khanicheh et al. |
| 2019/0038113 A1 | | 2/2019 | Chu |
| 2019/0134374 A1 | | 5/2019 | Korkuch et al. |
| 2020/0008838 A1 | | 1/2020 | Frey et al. |
| 2020/0107859 A1 | | 4/2020 | Zhu |
| 2020/0147349 A1 | | 5/2020 | Holt |
| 2020/0170559 A1 | | 6/2020 | Burkholz et al. |
| 2020/0188650 A1 | | 6/2020 | Al-Ali |
| 2020/0197682 A1 | | 6/2020 | Franklin et al. |
| 2021/0085927 A1 | | 3/2021 | Howell |
| 2021/0121661 A1 | | 4/2021 | Howell |
| 2021/0330941 A1 | | 10/2021 | Howell et al. |
| 2021/0332274 A1 | | 10/2021 | Hoshi et al. |
| 2021/0361915 A1 | | 11/2021 | Howell et al. |
| 2021/0402153 A1 | | 12/2021 | Howell et al. |
| 2022/0168548 A1 | | 6/2022 | Dong |
| 2022/0362524 A1 | | 11/2022 | Howell |
| 2022/0370762 A1 | | 11/2022 | Blanchard et al. |
| 2023/0039733 A1 | | 2/2023 | Howell |
| 2023/0041261 A1 | | 2/2023 | Howell |
| 2023/0043989 A1 | | 2/2023 | Howell |
| 2023/0064542 A1 | | 3/2023 | Howell |
| 2023/0086639 A1 | | 3/2023 | Howell |
| 2023/0096377 A1 | | 3/2023 | West et al. |
| 2023/0181878 A1 | | 6/2023 | Blanchard et al. |
| 2023/0201537 A1 | | 6/2023 | Howell et al. |
| 2023/0201538 A1 | | 6/2023 | Howell et al. |
| 2023/0218867 A1 | | 7/2023 | Howell et al. |
| 2023/0381481 A1 | | 11/2023 | Pizzato |
| 2024/0082549 A1 | | 3/2024 | Spataro et al. |
| 2024/0226507 A1 | | 7/2024 | Spataro |
| 2025/0375594 A1 | | 12/2025 | Lindekugel |
| 2026/0021276 A1 | | 1/2026 | Blanchard et al. |

FOREIGN PATENT DOCUMENTS

| | | |
|---|---|---|
| DE | 4136051 A1 | 7/1993 |
| DE | 19750090 A1 | 6/1999 |
| EP | 0067260 A1 | 12/1982 |
| EP | 0155331 A1 | 9/1985 |
| EP | 0499147 A2 | 8/1992 |
| EP | 0641571 A1 | 3/1995 |
| EP | 1338299 A1 | 8/2003 |
| EP | 3193813 A1 | 7/2017 |
| EP | 3473291 A1 | 4/2019 |
| JP | H02255156 A | 10/1990 |
| JP | H077971 Y2 | 3/1995 |
| JP | 2004254879 A | 9/2004 |
| JP | 2009232917 A | 10/2009 |
| JP | 5101359 B2 | 12/2012 |
| WO | 8906986 A1 | 8/1989 |
| WO | 95/09662 A1 | 4/1995 |
| WO | 98/10821 A1 | 3/1998 |
| WO | 9959651 A2 | 11/1999 |
| WO | 02/078776 A2 | 10/2002 |
| WO | 2005096778 A2 | 10/2005 |
| WO | 2009094089 A1 | 7/2009 |
| WO | 2011143621 A1 | 11/2011 |
| WO | 2012101089 A1 | 8/2012 |
| WO | 2013064215 A1 | 5/2013 |
| WO | 2015061172 A1 | 4/2015 |
| WO | 2016042544 A1 | 3/2016 |
| WO | 2016123278 A1 | 8/2016 |
| WO | 2016187063 A1 | 11/2016 |
| WO | 2020206280 A2 | 10/2020 |
| WO | 2021216902 A1 | 10/2021 |
| WO | 2021222116 A2 | 11/2021 |
| WO | 2022/204049 A1 | 9/2022 |
| WO | 2022246271 A2 | 11/2022 |
| WO | 2022245774 A3 | 12/2022 |
| WO | 2023014994 A1 | 2/2023 |
| WO | 2023018669 A1 | 2/2023 |
| WO | 2023018729 A1 | 2/2023 |
| WO | 2023018733 A1 | 2/2023 |
| WO | 2023028138 A2 | 3/2023 |
| WO | 2023049174 A1 | 3/2023 |
| WO | 2023091586 A1 | 5/2023 |
| WO | 2023114324 A1 | 6/2023 |
| WO | 2023122312 A1 | 6/2023 |
| WO | 2023129457 A1 | 7/2023 |
| WO | 2023137077 A1 | 7/2023 |
| WO | 2024059073 A1 | 3/2024 |
| WO | 2024151869 A1 | 7/2024 |
| WO | 2025259604 A1 | 12/2025 |

OTHER PUBLICATIONS

Lapalu et al. "Totally implantable port management: impact of positive pressure during needle withdrawal on catheter tip occlusion (an experimental study)" The Journal of Vascular Access 2010; 11: 46-51, 2010 Wichtig Editore, Original Article, 2010.

PCT/US2024/011269 filed Jan. 11, 2024 International Search Report and Written Opinion dated May 15, 2024.

U.S. Appl. No. 17/750,097, filed May 20, 2022 Notice of Allowance dated Jun. 27, 2025.

(56) References Cited

OTHER PUBLICATIONS

U.S. Appl. No. 17/883,490, filed Aug. 8, 2022 Non-Final Office Action dated Jul. 31, 2025.

U.S. Appl. No. 17/884,402, filed Aug. 9, 2022 Non-Final Office Action dated May 30, 2025.

U.S. Appl. No. 17/894,759, filed Aug. 24, 2022 Non-Final Office Action dated Jun. 16, 2025.

U.S. Appl. No. 17/949,734, filed Sep. 21, 2022 Non-Final Office Action dated Aug. 4, 2025.

PCT/US2022/030365 filed May 20, 2022 International Search Report and Written Opinion dated Apr. 4, 2023.

PCT/US2022/050280 filed Nov. 17, 2022 International Search Report and Written Opinion dated Apr. 17, 2023.

PCT/US2022/052884 filed Dec. 14, 2022 International Search Report and Written Opinion dated May 15, 2023.

PCT/US2022/053724 filed Dec. 21, 2022 International Search Report and Written Opinion dated May 10, 2023.

PCT/US2023/010623 filed Jan. 11, 2023, International Search Report and Written Opinion dated Jul. 6, 2023.

PCT/US2022/039742 filed Aug. 8, 2022 International Preliminary Report on Patentability dated Feb. 13, 2024.

PCT/US2022/041368 filed Aug. 24, 2022 International Preliminary Report on Patentability dated Feb. 27, 2024.

PCT/US2022/044242 filed Sep. 21, 2022 International Preliminary Report on Patentability dated Mar. 26, 2024.

PCT/US2022/053887 filed Dec. 22, 2022 International Search Report and Written Opinion dated May 8, 2023.

PCT/US2022/039742 filed Aug. 8, 2022 International Search Report and Written Opinion dated Dec. 21, 2022.

PCT/US2022/039852 filed Aug. 9, 2022 International Search Report and Written Opinion dated Dec. 6, 2022.

PCT/US2022/039861 filed Aug. 9, 2022, International Search Report and Written Opinion dated Jan. 5, 2023.

PCT/US2022/041368 filed Aug. 24, 2022 International Search Report and Written Opinion dated Mar. 21, 2023.

PCT/US2022/044242 filed Sep. 21, 2022 International Search Report and Written Opinion dated Feb. 8, 2023.

PCT/US2022/021187 filed Mar. 21, 2022 International Search Report and Written Opinion dated Jun. 17, 2022.

PCT/US2022/029561 filed May 17, 2022 International Search Report and Written Opinion dated Nov. 9, 2022.

PCT/US2023/032545 filed Sep. 12, 2023 International Search Report and Written Opinion dated Feb. 13, 2024.

U.S. Appl. No. 17/700,152, filed Mar. 21, 2022 Restriction Requirement dated Apr. 29, 2025.

U.S. Appl. No. 17/700,152, filed Mar. 21, 2022 Restriction Requirement dated Jan. 31, 2025.

U.S. Appl. No. 17/746,113, filed May 17, 2022 Non-Final Office Action dated Apr. 7, 2025.

U.S. Appl. No. 17/746,113, filed May 17, 2022 Restriction Requirement dated Dec. 11, 2024.

U.S. Appl. No. 17/750,097, filed May 20, 2022 Restriction Requirement dated Mar. 20, 2025.

U.S. Appl. No. 17/884,307, filed Aug. 9, 2022 Non-Final Office Action dated Apr. 2, 2025.

PCT/US2025/032881 filed Jun. 9, 2025 International Search Report and Written Opinion dated Sep. 24, 2025.

U.S. Appl. No. 17/700,152, filed Mar. 21, 2022 Non-Final Office Action dated Aug. 14, 2025.

U.S. Appl. No. 17/884,307, filed Aug. 9, 2022 Final Office Action dated Oct. 23, 2025.

U.S. Appl. No. 17/884,402, filed Aug. 9, 2022 Notice of Allowance dated Sep. 10, 2025.

U.S. Appl. No. 17/894,759, filed Aug. 24, 2022 Final Office Action dated Sep. 24, 2025.

U.S. Appl. No. 18/081,491, filed Dec. 14, 2022 Non-Final Office Action dated Aug. 22, 2025.

U.S. Appl. No. 18/087,676, filed Dec. 21, 2022 Non-Final Office Action dated Oct. 31, 2025.

U.S. Appl. No. 18/087,676, filed Dec. 22, 2022 Restriction Requirement dated Oct. 8, 2025.

U.S. Appl. No. 17/700,152 filed Mar. 21, 2022 Final Office Action dated Feb. 12, 2026.

U.S. Appl. No. 17/883,490, filed Aug. 8, 2022 Final Office Action dated Dec. 22, 2025.

U.S. Appl. No. 17/894,759, filed Aug. 24, 2022 Notice of Allowance dated Dec. 16, 2025.

U.S. Appl. No. 17/949,734, filed Sep. 21, 2022 Final Office Action dated Feb. 5, 2026.

U.S. Appl. No. 18/081,491, filed Dec. 14, 2022 Final Office Action dated Jan. 12, 2026.

U.S. Appl. No. 18/095,968, filed Jan. 11, 2023 Restriction Requirement dated Nov. 24, 2025.

U.S. Appl. No. 18/087,676, filed Dec. 22, 2022 Non-Final Office Action dated Mar. 6, 2026.

U.S. Appl. No. 18/095,968, filed Jan. 11, 2023 Non-Final Office Action dated Mar. 23, 2026.

U.S. Appl. No. 18/410,781, filed Jan. 11, 2024 Non-Final Office Action dated Mar. 25, 2026.

U.S. Appl. No. 17/883,490, filed Aug. 8, 2022 Advisory Action dated Mar. 26, 2026.

* cited by examiner

PROXIMAL

DISTAL

TOP

BOTTOM

SPLITTABLE NEEDLE FOR CATHETER PLACEMENT SYSTEM

PRIORITY

This application claims the benefit of priority to U.S. Provisional Application No. 63/281,008, filed Nov. 18, 2021, which is incorporated by reference in its entirety into this application.

BACKGROUND

Central venous catheter ("CVCs") are commonly introduced into patients and advanced through their vasculatures by way of the Seldinger technique. The Seldinger technique utilizes a number of steps and medical devices (e.g., a needle, a scalpel, a guidewire, an introducer sheath, a dilator, a CVC, etc.). While the Seldinger technique is effective, the number of steps are time consuming, handling the number of medical devices is awkward, and both of the foregoing can lead to patient trauma or increased risk of infection. There is a relatively high potential for touch contamination due to the number of medical devices that need to be interchanged during the Seldinger technique. As such, advanced catheter placement systems have been developed to reduce the number of steps and medical devices involved in placing a catheter, such as a CVC, into a patient.

Some of these advanced catheter placement systems include accessing a vasculature with a needle and stabilizing the access site with a guidewire. Preferably, a distal portion of the guidewire is disposed within a lumen of the needle and is advanced concurrently. As such, the guidewire is already in place once the vasculature is accessed, expediting the process. Further, a proximal portion of the guidewire can include a catheter disposed thereon (termed "preloaded") to further expedite advancing the catheter over the guidewire and into the vasculature. Problems can arise however with how to remove the needle safely without dislodging a distal tip of the guidewire and without removing the catheter from a proximal portion of the guidewire Disclosed herein are advanced catheter placement systems and associated methods for removing the needle from the access site without disturbing the position of the guidewire.

SUMMARY

Disclosed herein is a catheter placement system including, a needle defining a needle lumen, a guidewire extending through a portion of the needle lumen, a housing defining a needle channel and having a portion of the needle slidably engaged therewith, and a splitter system disposed within the housing and configured to split the needle longitudinally as the needle is withdrawn proximally through the needle channel.

In some embodiments, the needle is supported at a proximal end by one or both of a needle hub and a syringe system, the syringe system configured to draw a fluid flow proximally through the needle lumen.

In some embodiments, the housing further includes a guidewire channel communicating with the needle channel, the guidewire channel aligned with an aperture disposed in a wall of the needle and communicating with the needle lumen, a portion of the guidewire extending through the guidewire channel, through the aperture and into the needle lumen.

In some embodiments, the splitter system includes a wedge disposed distally of the aperture and configured to split the needle along a longitudinal axis.

In some embodiments, the needle further includes a tear line extending longitudinally and aligned with the splitter system, the tear line configured to facilitate separation of the needle therealong.

In some embodiments, the splitter system further includes a valve extending between an outer surface of the needle and an inner surface of the needle channel and configured to mitigate fluid leakage to or from the needle lumen, the splitter system configured to split the valve as the needle is withdrawn proximally.

In some embodiments, the catheter placement further includes a needle safety system having one or both of a first tape and a second tape configured to encapsulate one or both of a first portion and a second portion of the needle after the needle has been split by the splitter system.

In some embodiments, one or both of the first tape and the second tape are disposed within the housing in a rolled configuration and are configured to transition to an unrolled configuration as the needle is withdrawn proximally from the housing.

In some embodiments, wherein a top edge of the first tape is configured to adhere to a top edge of the second tape, and a bottom edge of the first tape is configured to adhere to a bottom edge of the second tape to encapsulate the first portion and the second portion of the needle therebetween.

In some embodiments, the first tape in the unrolled configuration is designed to encapsulate to the first portion of the needle, and the second tape in the unrolled configuration is designed to encapsulate the second portion of the needle.

In some embodiments, wherein a top edge of the first tape is configured to overlap a bottom edge of the first tape to encapsulate one or both of the first portion and the second portion of the needle.

In some embodiments, wherein the first tape is adhered to an inner surface of the first portion of the needle, a distal end of the first tape configured to fold outwards and adhere to an outer surface of the first portion, and wherein the second tape is adhered to an inner surface of the second portion of the needle, a distal end of the first tape configured to fold outwards and adhere to an outer surface of the second portion.

In some embodiments, wherein one or both of the first tape and the second tape include a first material, the first material including one or more of a plastic, polymer, metal, alloy, composite, KEVLAR®, or a puncture-resistant material.

In some embodiments, wherein one or both of the first tape and the second tape include a reinforcement portion.

In some embodiments, wherein the reinforcement portion includes one of a thickened portion or a second material different from the first material, the second material including one of a plastic, polymer, metal, alloy, composite, KEVLAR®, or a puncture-resistant material.

In some embodiments, the catheter placement further includes a catheter disposed on a proximal portion of the guidewire.

In some embodiments, the catheter includes a first section disposed distally and defining a first diameter, a second section disposed proximally and defining a second diameter, larger than the first diameter, and a transition section extending therebetween.

In some embodiments, the first section defines a single lumen and the second section defines two or more lumen.

Also disclosed is a method of encapsulating a needle of a catheter placement system including, accessing a vasculature of a patient with a needle, advancing a portion of a guidewire through a lumen of the needle, withdrawing the needle proximally through a channel of a housing, splitting the needle longitudinally into a first needle half and a second needle half, disengaging the guidewire from the needle by passing the portion of the guidewire longitudinally between the first needle half and the second needle half, and engaging one or both of the first needle half and the second needle half with one or both of a first adhesive tape and a second adhesive tape.

In some embodiments, the needle further includes a tear line extending longitudinally and configured to facilitate separating the needle longitudinally into the first needle half and the second needle half.

In some embodiments, the method further includes advancing the portion of the guidewire through an aperture extending through a side wall of the needle and communicating with the needle lumen.

In some embodiments, the method further includes withdrawing the needle over a splitter wedge to split the needle into the first needle half and the second needle half.

In some embodiments, the method further includes adhering a top edge of the first adhesive tape to a top edge of the second adhesive tape, and adhering a bottom edge of the first adhesive tape to a bottom edge of the second adhesive tape to encapsulate the first needle half and the second needle half between the first adhesive tape and the second adhesive tape.

In some embodiments, the method further includes adhering the first adhesive tape to the first needle half, a top edge of the first adhesive tape extending over a top edge of the first needle half to adhere to an inner surface thereof, and a bottom edge of the first adhesive tape extending over a bottom edge of the first needle half to adhere to an inner surface thereof.

In some embodiments, the method further includes adhering the second adhesive tape to the second needle half, a top edge of the second adhesive tape extending over a top edge of the second needle half to adhere to an inner surface thereof, and a bottom edge of the second adhesive tape extending over a bottom edge of the second needle half to adhere to an inner surface thereof.

In some embodiments, the method further includes adhering the first adhesive tape to one or both of the first needle half and the second needle half, a top edge of the first adhesive tape overlapping a bottom edge of the first adhesive tape.

In some embodiments, the method further includes adhering the first adhesive tape to an inner surface of the first needle half, and folding a distal portion of the first adhesive tape outwards to engage an outer surface of the first needle half, and adhering the second adhesive tape to an inner surface of the second needle half, and folding a distal portion of the second adhesive tape outwards to engage an outer surface of the second needle half.

In some embodiments, one or both of the first adhesive tape and the second adhesive tape include a first material, the first material including one or more of a plastic, polymer, metal, alloy, composite, KEVLAR®, or a puncture-resistant material.

In some embodiments, one or both of the first adhesive tape and the second adhesive tape include a reinforcement portion having one of a thickened portion or a second material different from the first material, the second material including one of a plastic, polymer, metal, alloy, composite, KEVLAR®, or a puncture-resistant material.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1A:
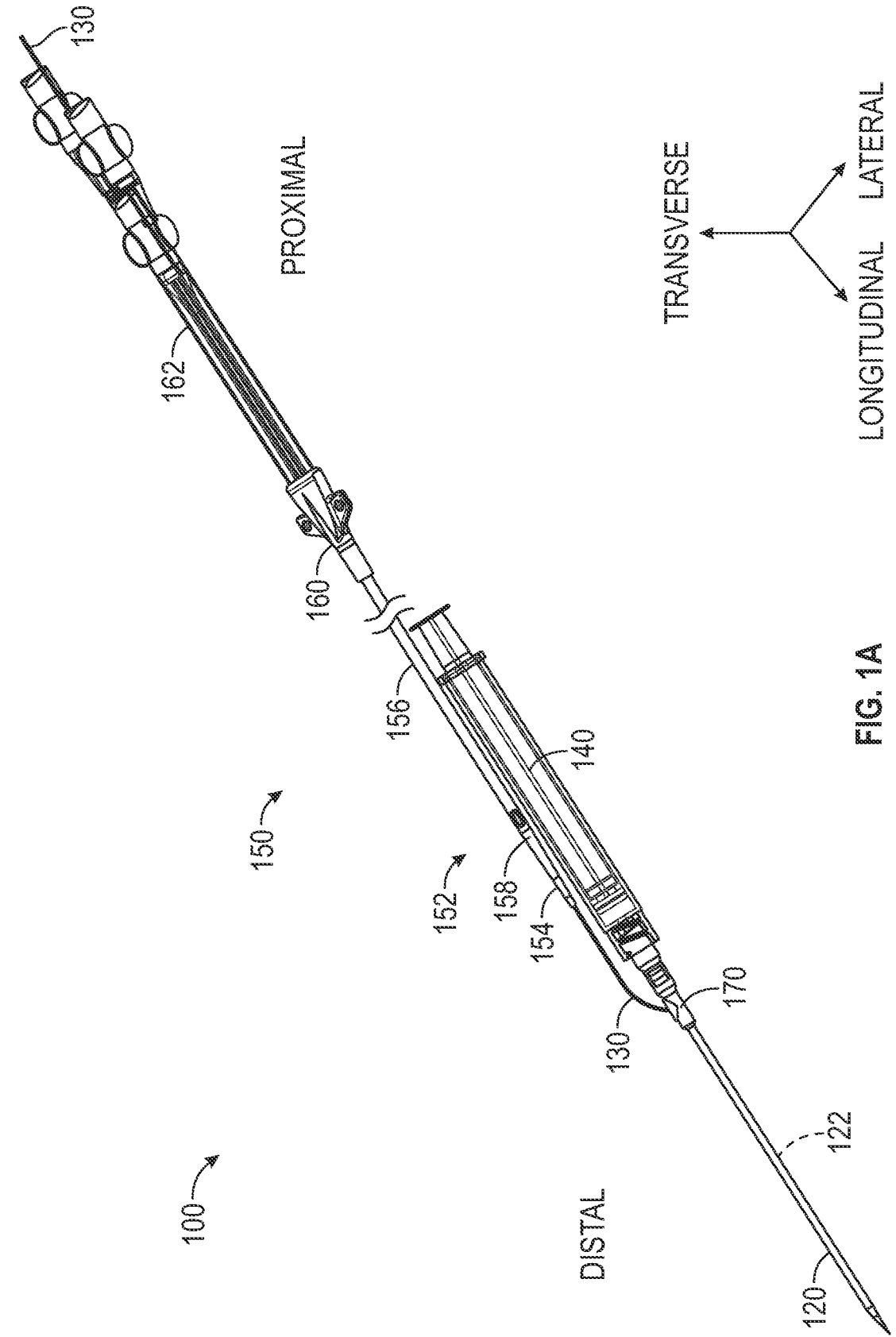
FIG. 1A shows a perspective view of a catheter placement system in an unfolded configuration, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

In the following description, the terms "or" and "and/or" as used herein are to be interpreted as inclusive or meaning any one or any combination. As an example, "A, B or C" or "A, B and/or C" mean "any of the following, A, B, C, A and B, A and C, B and C, A, B and C." An exception to this definition will occur only when a combination of elements, components, functions, steps or acts are in some way inherently mutually exclusive.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

To assist in the description of embodiments described herein, as shown in FIG. 1A, a longitudinal axis extends substantially parallel to an axial length of the needle. A lateral axis extends normal to the longitudinal axis, and a transverse axis extends normal to both the longitudinal and lateral axes.

Unless defined otherwise, all technical and scientific terms used herein have the same meaning as commonly understood by those of ordinary skill in the art.

Figure 1B:
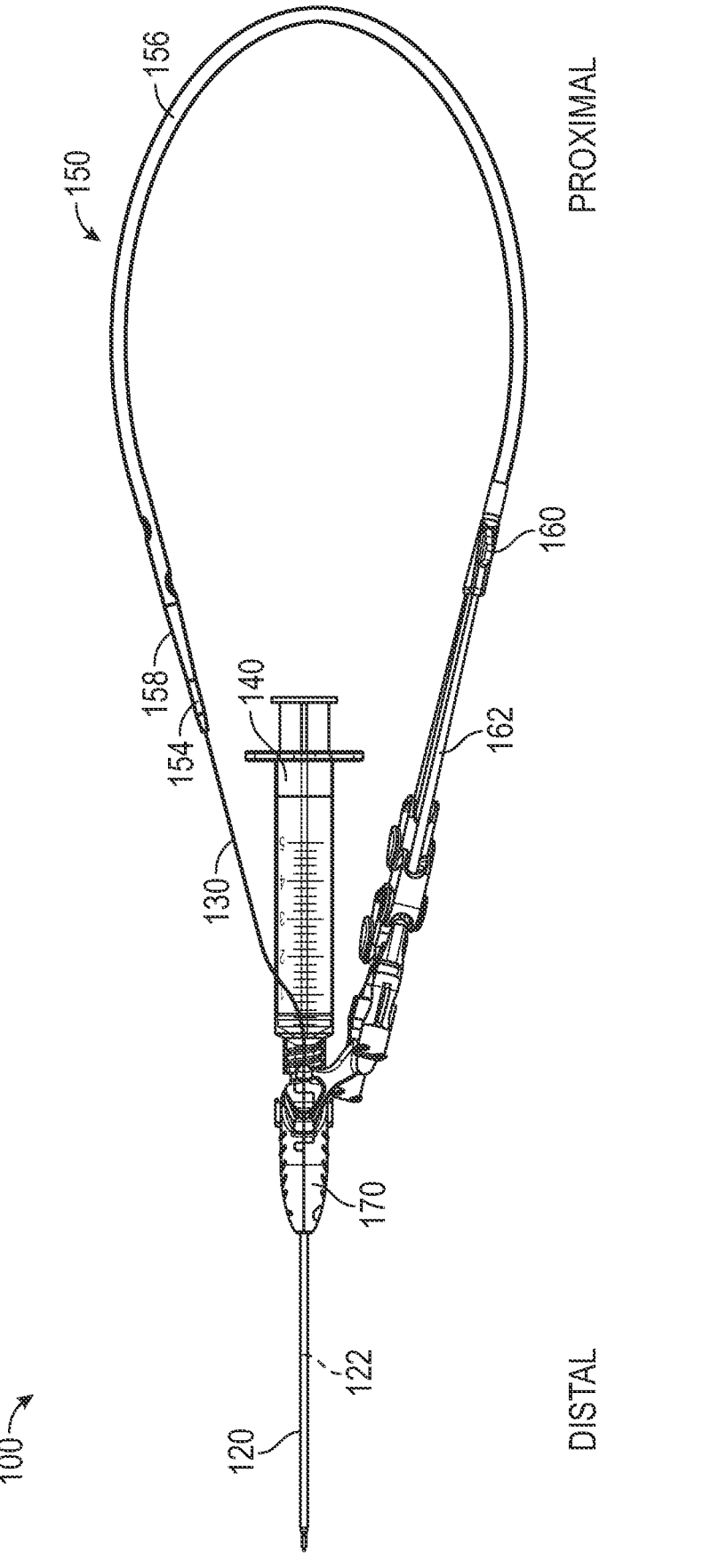
FIG. 1B shows a plan view of a catheter placement system in a folded configuration ready for use, in accordance with embodiments disclosed herein.
Figure 1C:
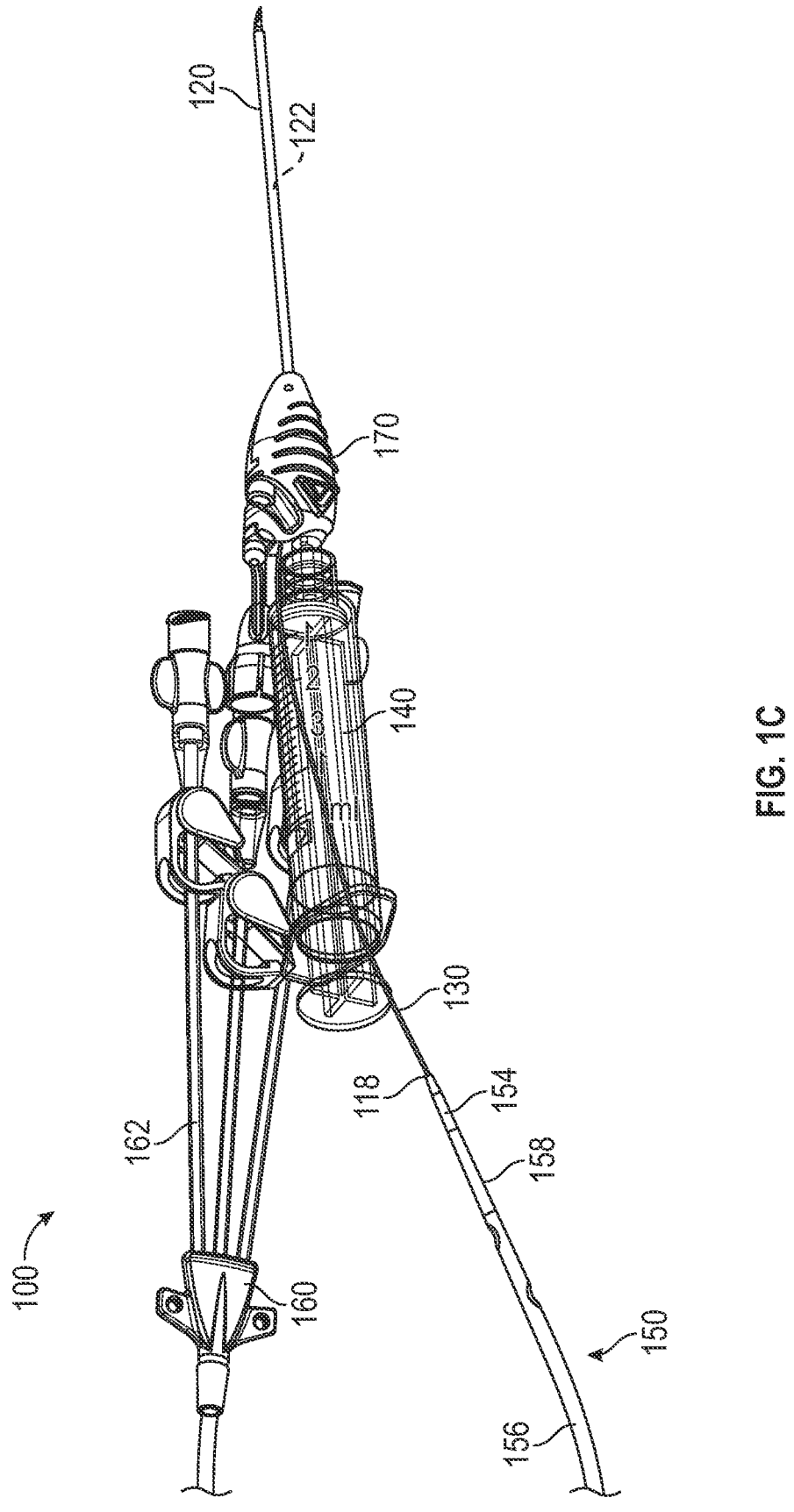
FIG. 1C shows a perspective view of a catheter placement system in a folded configuration, in accordance with embodiments disclosed herein.

FIGS. 1A-1C show an exemplary advanced catheter placement system ("system") 100, generally including a needle 120, a guidewire 130, a syringe system 140, a catheter 150, and a needle housing ("housing") 170. FIG. 1A shows the system 100 in an unfolded configuration for ease of illustration. FIG. 1B shows a plan view of the system 100 in a folded configuration ready for use. FIG. 1C shows a perspective view the system 100 in a folded configuration. In an embodiment the catheter placement system 100 can be a Rapidly Insertable Central Catheter (RICC) placement system 100 configured to place a RICC 150. However, it will be appreciated that other catheter placement systems configured to place other types of catheters are also contemplated. Exemplary catheters 150 can also include peripheral intravenous (PIV) catheters, peripherally inserted central catheter (PICC), central venous catheters (CVC), midline catheters, dialysis catheters, single lumen catheters, multi-lumen catheters, or the like.

In an embodiment, the catheter 150 can generally include a catheter body 152 supported at a proximal end by a catheter hub ("hub") 160. The hub 160 can include one or more extension legs 162 extending proximally therefrom. Each extension leg of the one or more extension legs 162 can be in fluid communication with a lumen of the catheter body 152. The catheter body 152 can include a first section 154 disposed distally, a second section 156 disposed proximally, and a transition section 158 disposed therebetween. The first section 154 can define a single lumen and have a first outer diameter, the second section 156 can define two or more lumen and can have a second diameter larger than the first diameter. The transition section 158 disposed between the first section 154 and the second section 156 can define a tapered shape extending from the first diameter of the first section to the second diameter of the second section. A guidewire 130 can extend through a lumen of the catheter 150 from a proximal end of an extension leg 162, to a distal tip of the first section 154.

Figure 2:
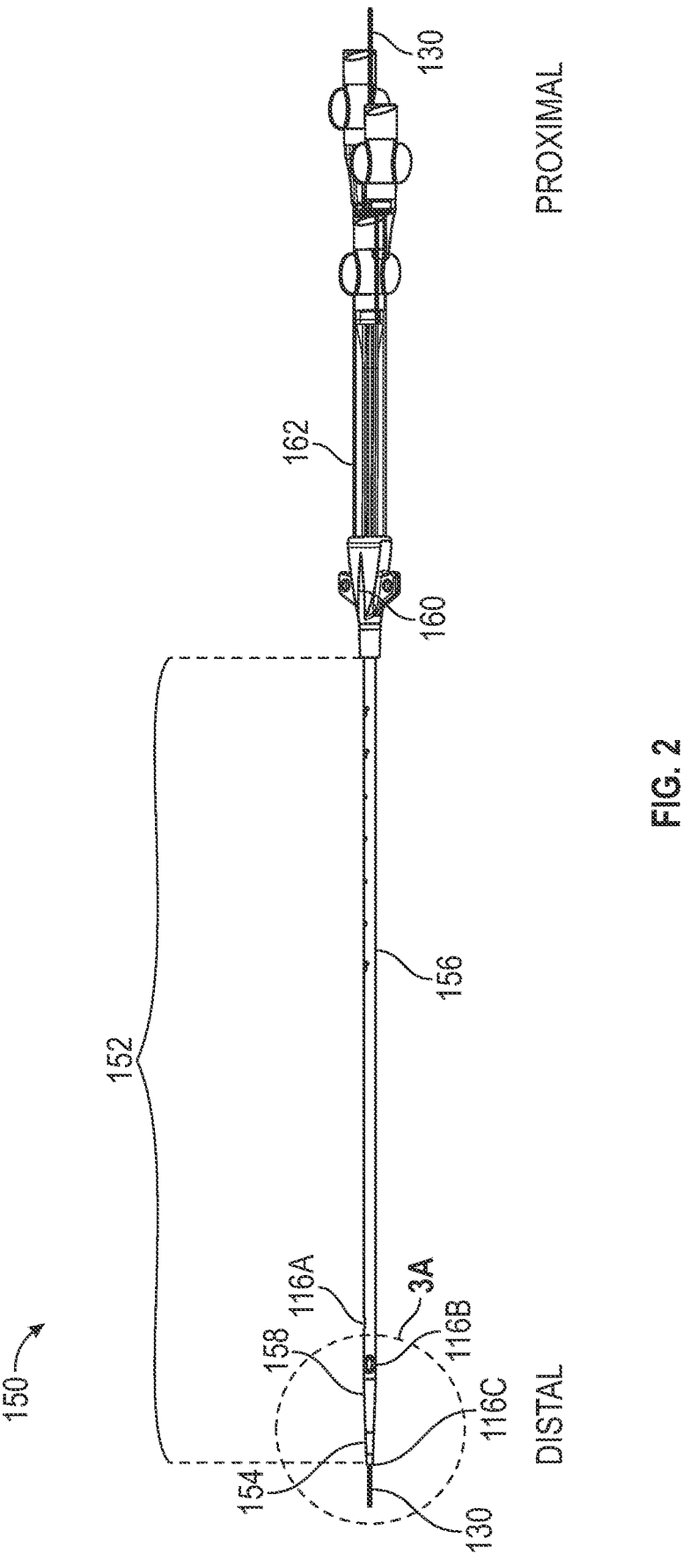
FIG. 2 shows a side view of a catheter of a catheter placement system in an unfolded configuration, in accordance with embodiments disclosed herein.

FIG. 2 shows further details of an exemplary catheter 150 of the system 100. As described herein, different sections of the catheter 150 are required to perform different functions and as such are required to display different mechanical properties. For example, the first section 154 and the transition section 158 can provide more rigid mechanical properties or harder durometer material relative to the second section 156. As such, the first section 154 and transition section 158 can withstand greater axial forces without kinking or collapsing, as these sections are urged distally, forming and dilating the insertion site. The second section 156 can be formed of a softer durometer, or a more compliant material to facilitate negotiating the second section 156 through tortuous vascular pathways.

Figure 3A:
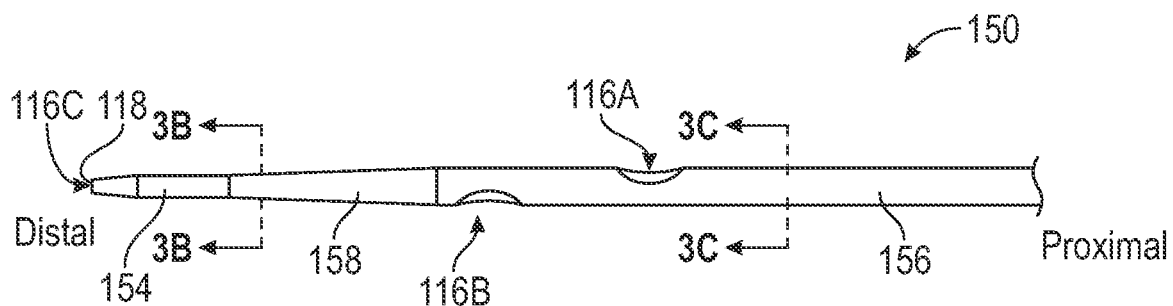
FIG. 3A shows close up detail of a distal portion of the catheter of FIG. 2, in accordance with embodiments disclosed herein.
Figure 3B:
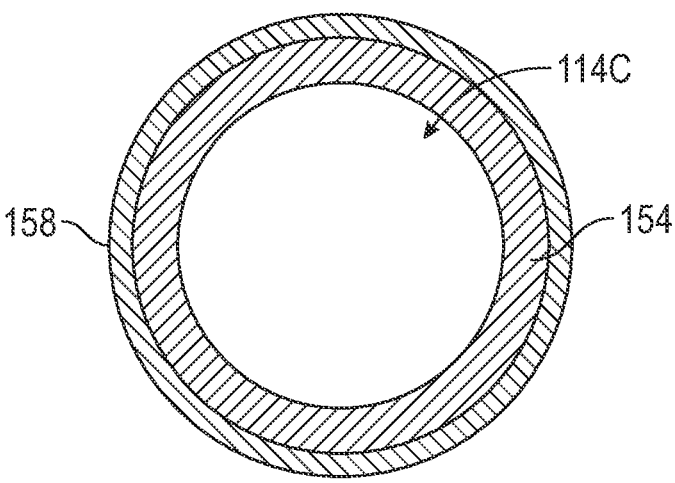
FIGS. 3B-3C show cross-section views of the catheter of FIG. 3A, in accordance with embodiments disclosed herein.
Figure 3C:
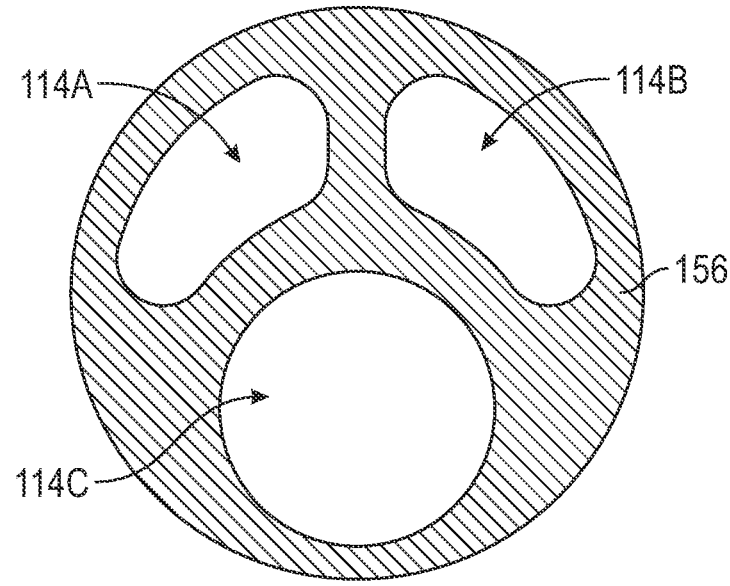

FIGS. 3A-3C show further details of a distal portion of the catheter 150, including the first section 154, the second section 156, and the transition section 158. In an embodiment, the second section 156 can include a proximal lumen 114A terminating at a proximal lumen aperture 116A, and a medial lumen 114B terminating at a medial lumen aperture 116B. Each of the proximal lumen aperture 116A and the medial lumen aperture 116B can extend through a side wall of the second section 156. Each of the proximal lumen aperture 116A and the medial lumen aperture 116B can be disposed proximally of the transition section 158. The proximal lumen aperture 116A can be disposed proximally of the medial lumen aperture 116B. In an embodiment, the proximal lumen aperture 116A and the medial lumen aperture 116B can be disposed equidistant from the distal tip 118 of the catheter 150.

FIG. 3B shows a cross section view of the catheter body 152 at point "A" of FIG. 3A. As shown, the first section 154 can define a single lumen and a relatively smaller outer diameter. In an embodiment, a proximal portion of the first section 154 can be received within a distal portion of the transition section 158. A distal lumen 114C of the catheter 150 can extend to a distal tip 118 of the catheter 150 and can communicate with a distal lumen aperture 116C. FIG. 3C shows a cross section view of the second section 156 at point "B" of FIG. 3A, showing the proximal lumen 114A, medial lumen 114B and distal lumen 114C.

Figure 4:
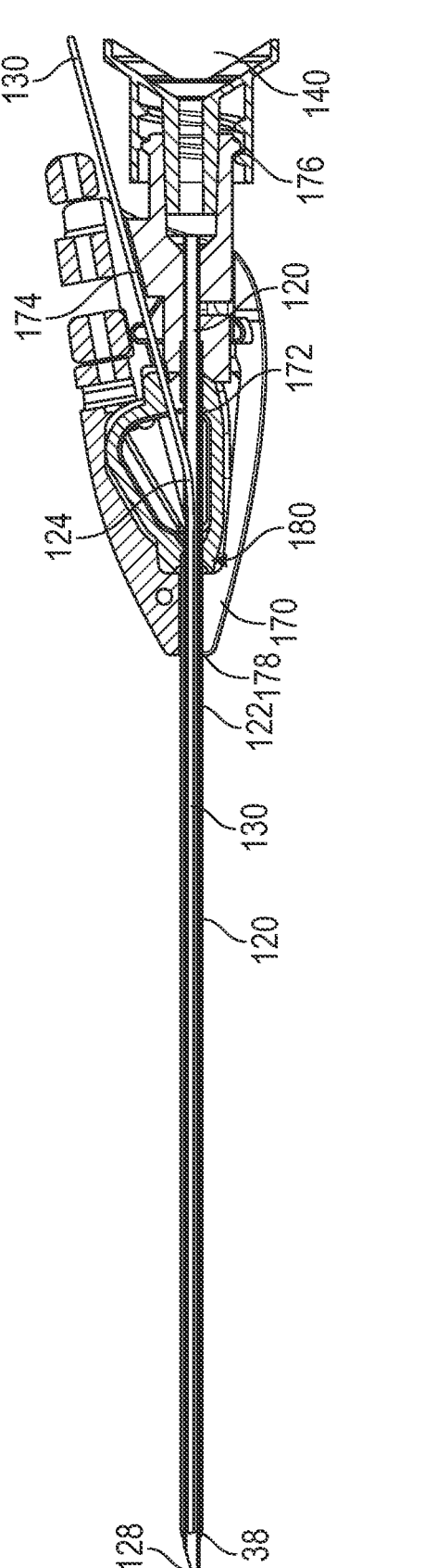
FIG. 4 shows a longitudinal cross-section view of a distal portion of a catheter placement system, in accordance with embodiments disclosed herein.

FIG. 4 shows a longitudinal cross-section view of a distal portion of a catheter placement system 100 including the needle 120, guidewire 130, a distal portion of the syringe system 140, and a needle housing ("housing") 170 including a needle splitter system 180, as described in more detail herein. In an embodiment, a proximal end of the needle 120 can be supported by a needle hub which can be coupled to, and supported by, a distal end of the syringe system 140. The syringe system 140 can be in fluid communication with the needle lumen 122. The syringe system 140 can be configured to form a vacuum within the needle lumen 122 and draw a fluid flow proximally therethrough. In an embodiment, the needle 120 can include a guidewire aperture 124 disposed in a wall of the needle 120 and communicating with a needle lumen 122. A distal portion of the guidewire 130 can extend through the guidewire aperture 124 and into the needle lumen 122. In an embodiment, a distal tip 138 of the guidewire 130 can be disposed proximate a distal tip 128 of the needle 120. As such, once the needle 120 accesses the vasculature, the distal tip 138 of the guidewire 130 can be positioned within the vasculature, expediting the placement of the catheter 150.

In an embodiment, the catheter placement system 100 can include a housing 170. The housing 170 can include a needle channel 172 extending between a proximal end 176 and a distal end 178 of the housing 170. The housing 170 can further include a guidewire channel 174 communicating with the needle channel 172 and extending at an angle therefrom. A portion of the needle 120 can slidably engage the needle channel 172. Further, the proximal end 176 of the housing can releasably engage one or both of a needle hub and a distal portion of the syringe system 140. When the housing 170 is engaged with the syringe system 140 the guidewire aperture 124 of the needle 120 can align with the guidewire channel 174 of the housing 170. As such, the guidewire 130 can extend through the guidewire channel 174 of the housing 170, through the guidewire aperture 124 of the needle 120 and into the needle lumen 122.

Figure 5A:
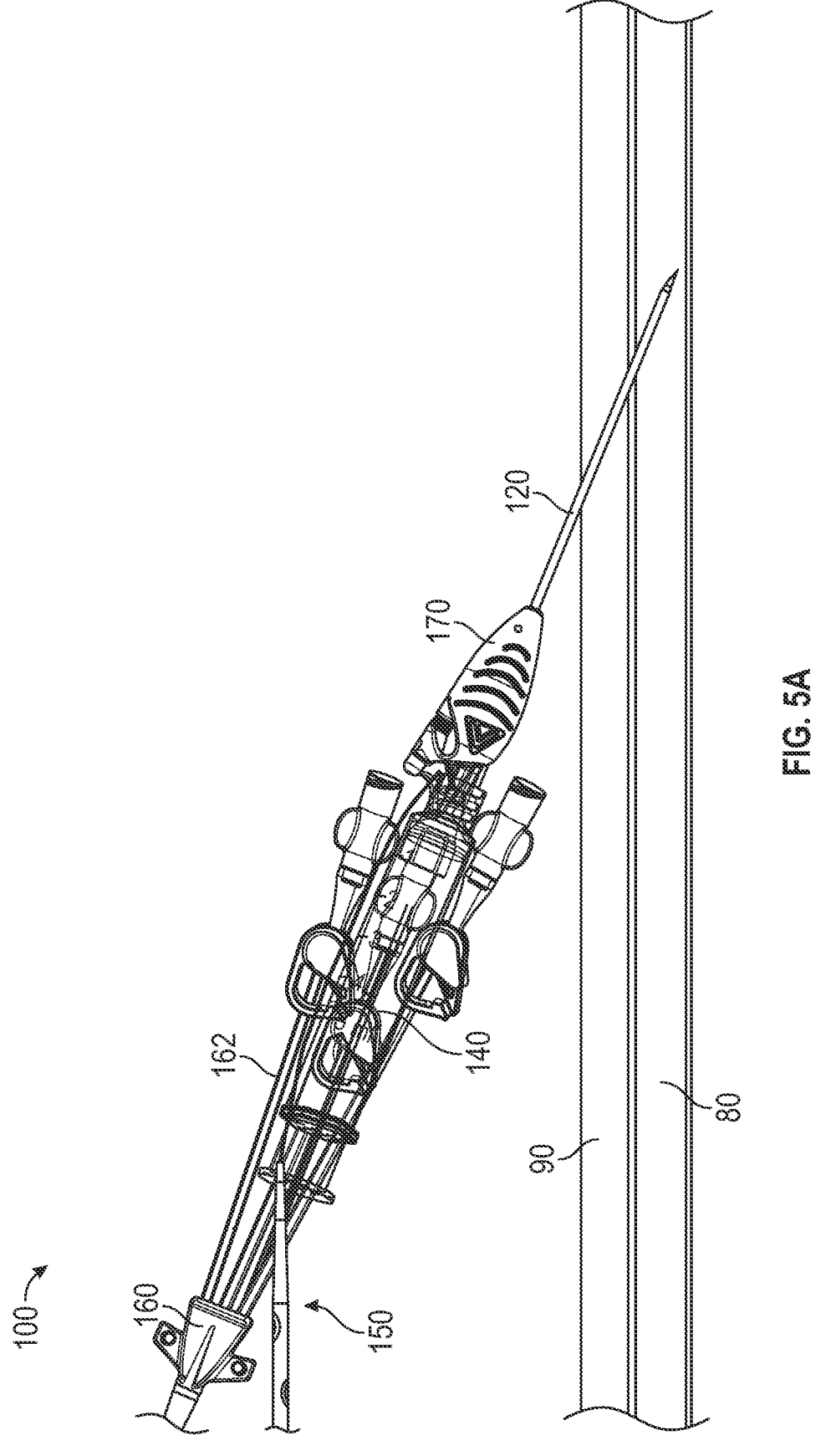
FIGS. 5A-5E show an exemplary method of use for a catheter placement system, in accordance with embodiments disclosed herein.
Figure 5B:
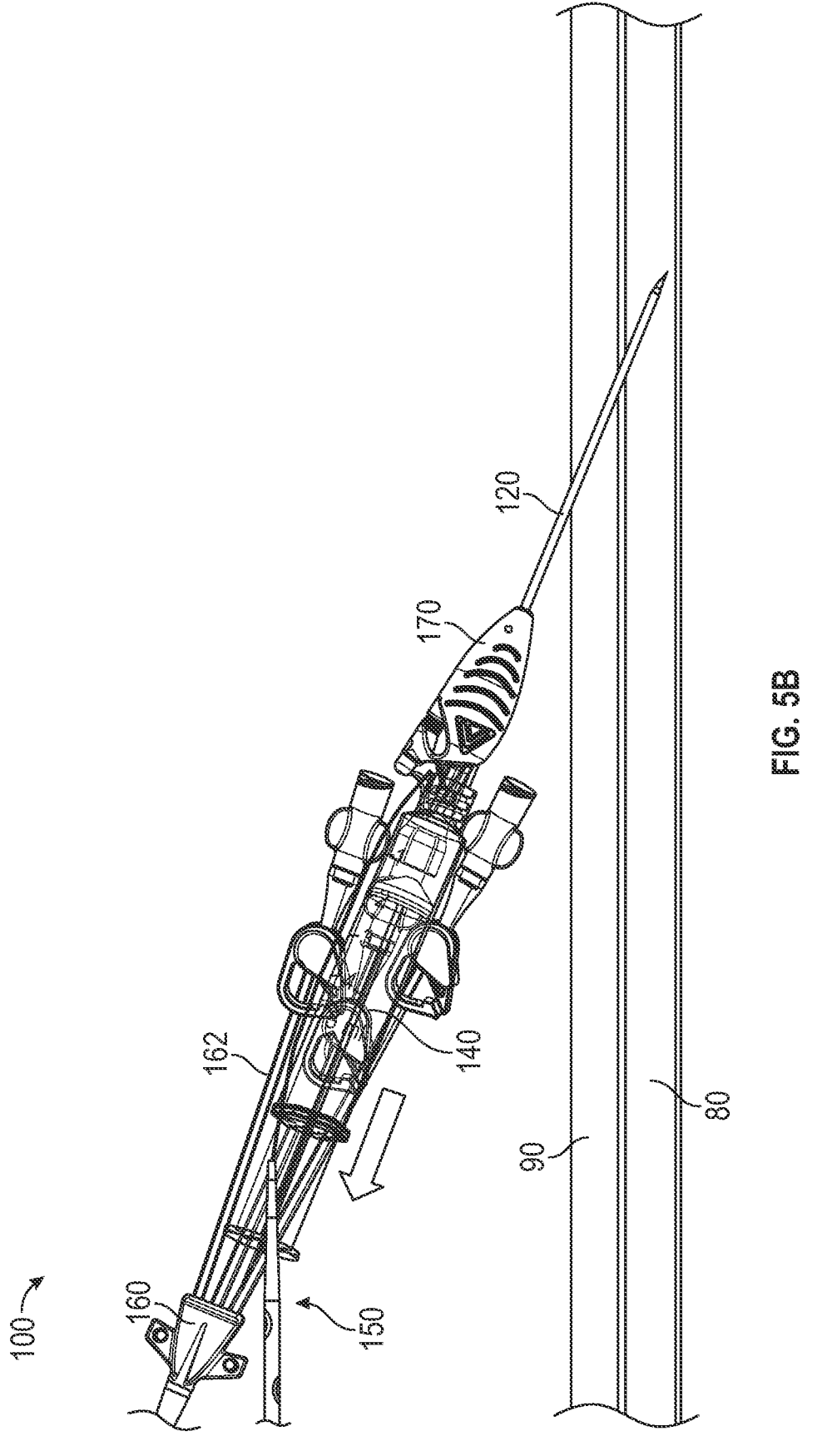
Figure 5C:
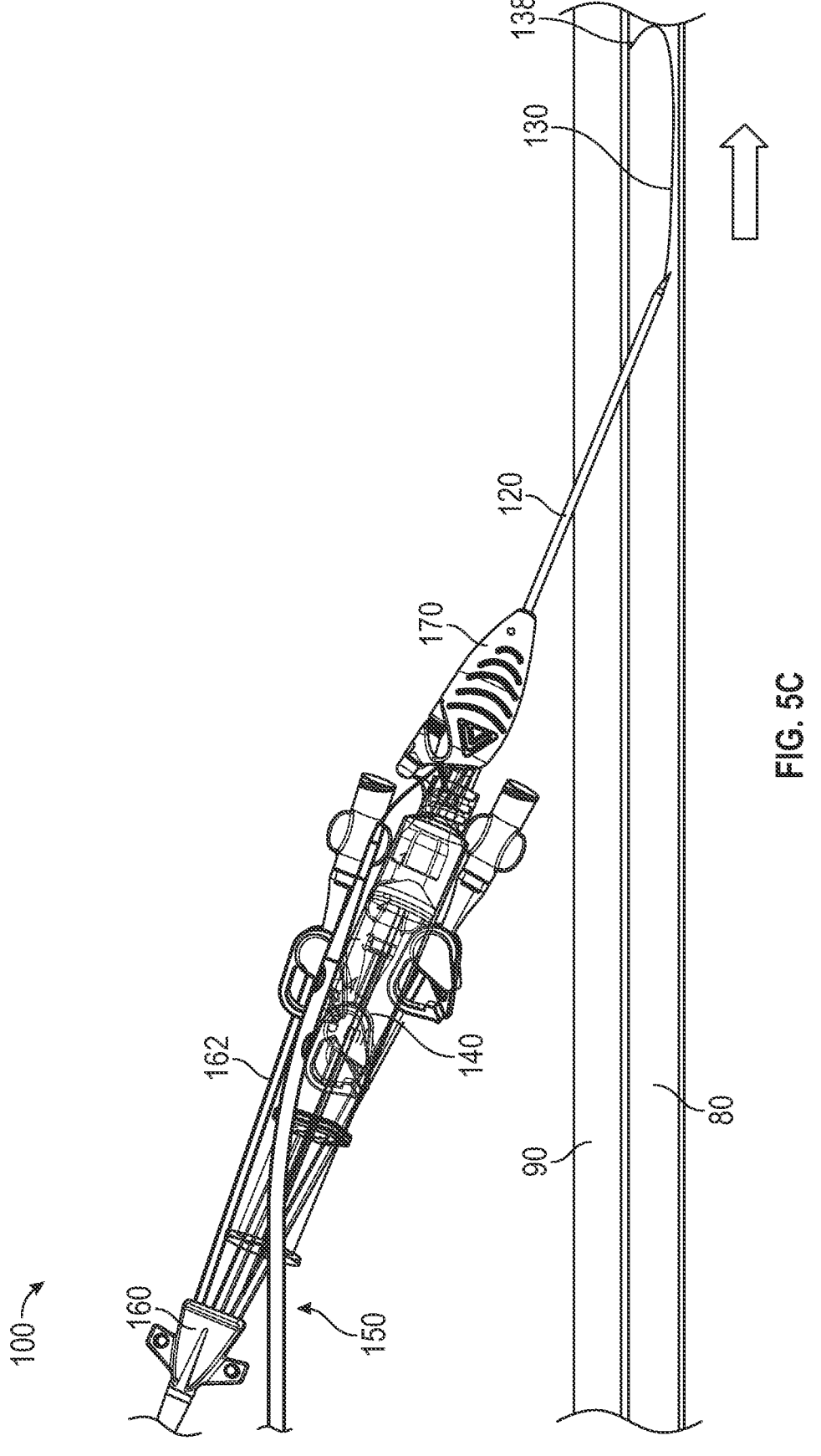

FIGS. 5A-5E show an exemplary method of placing a catheter 150 using the catheter placement system 100. As shown in FIG. 5A, the needle 120 can penetrate surface tissues 90 of the patient and access a vasculature 80, forming an insertion site. As shown in FIG. 5B, a syringe system 140, or similar device can form a vacuum and draw a fluid flow proximally through a needle lumen 122. A user can observe a color or pulsatile flow and confirm correct vascular access. Where incorrect vascular access is confirmed, the needle 120 can be withdrawn and the insertion site can be closed. As shown in FIG. 5C, once correct vascular access has been confirmed, the guidewire 130 can then be advanced through the needle lumen 122 and into the vasculature 80 to maintain patency of the insertion site.

Figure 5D:
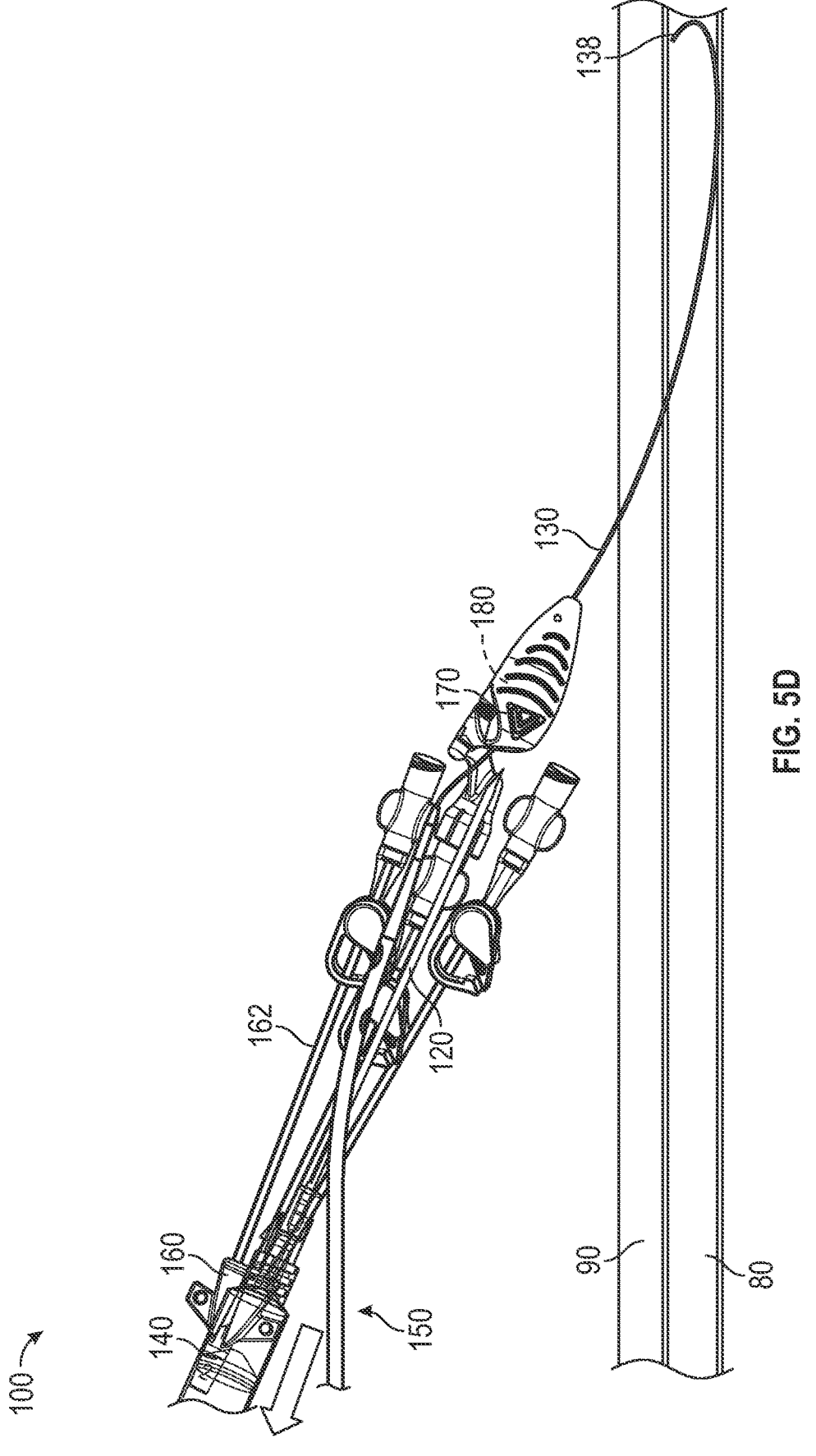

As shown in FIG. 5D, the needle 120 and syringe system 140 assembly can be withdrawn proximally to disengage the needle 120 from the guidewire 130 while leaving a distal portion of the guidewire 130 in place within the vasculature 80. As described in more detail herein, the housing 170 can include a splitter system 180 configured to split the needle 120 longitudinally, as the needle 120 is withdrawn proximally. A portion of the guidewire 130 can pass between the two halves of the needle 120 to allow the needle 120 to disengage the guidewire 130.

Figure 5E:
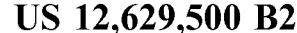

As shown in FIG. 5E, with the needle 120 and syringe system 140 assembly disengaged from the guidewire 130, the catheter 150 can then be advanced over the guidewire 130 and into the vasculature. The first section 154 of the catheter 150, having only a single lumen and defining a relatively smaller outer diameter, can enter the vasculature 80 over the guidewire 130, anchoring the insertion site. The transition section 158 can then be urged distally, dilating the insertion site to allow the relatively larger diameter second section 156, defining two or more lumen, to enter the vasculature 80. Once the catheter 150 has been placed, the guidewire 130 can be withdrawn proximally.

Further details and embodiments of RICC systems 100 can be found, for example, in U.S. Pat. No. 10,376,675, U.S. 2019/0255294, U.S. 2021/0069471, U.S. 2021/0085927, U.S. 2021/0113809, U.S. 2021/0113810, U.S. 2021/0121661, U.S. 2021/0228843, U. S. 2021/0283368, U. S. 2021/0283381, U. S. 2021/0322729, U. S. 2021/0330941, U. S. 2021/0330942, U. S. 2021/0361915, U. S. 2021/0379336, U. S. 2021/0402142, U. S. 2021/0402149, U. S. 2021/0402153, U. S. 2021/0121667, U. S. 2022/0001138, U. S. 2022/0032013, U. S. 2022/0032014, U. S. 2022/0062528, U. S. 2022/0126064, U.S. 2022/0152368, U.S. 2022/0176081, U.S. 2022/0176082, U.S. 2022/0193376, U.S. 2022/0193377, U.S. 2022/0193378, U.S. 2022/0193379, and U.S. 2022/0296862, each of which is incorporated by reference in its entirety into this application.

Figures 6A, 6B:
FIG. 6A shows a side cross-section view of a needle for a catheter placement system prior to needle removal, in accordance with embodiments disclosed herein.
FIG. 6B shows a plan cross-section view of a needle for a catheter placement system prior to needle removal, in accordance with embodiments disclosed herein.
Figure 6C:
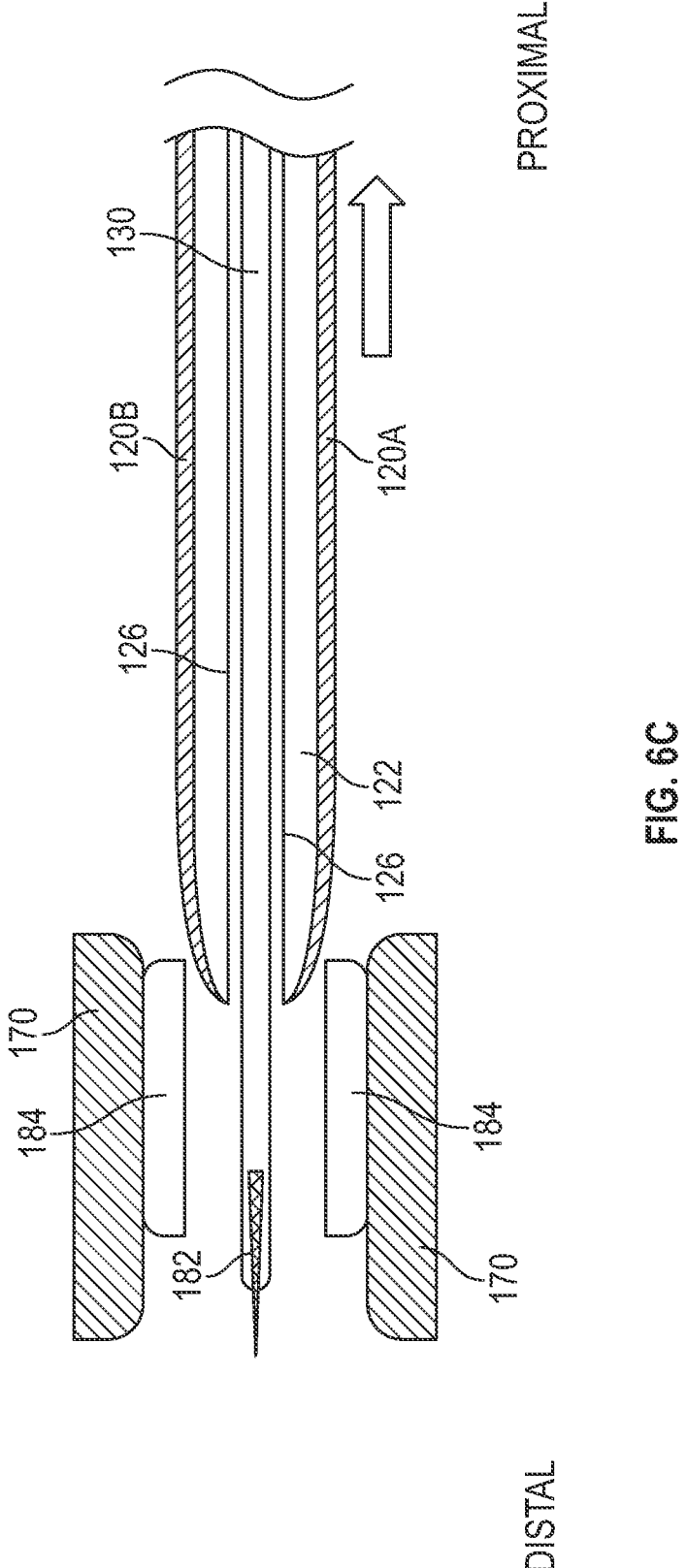
FIG. 6C shows a plan cross-section view of a needle for a catheter placement system after needle removal, in accordance with embodiments disclosed herein.

In an embodiment, as shown in FIGS. 6A-6C, the catheter placement system 100 can include a splittable needle 120 and splitter system 180 configured to separate the needle 120 along a longitudinal axis into a first portion 120A and a second portion 120B. As such, the guidewire 130 can pass between the first portion 120A and the second portion 120B of the needle 120 to facilitate disengaging the needle 120 from the guidewire 130 during placement, (e.g. FIG. 5D). Advantageously, the catheter placement system 100 can quick remove the needle 120 without disturbing the position of the guidewire 130. Further, the needle 120 can be removed while the catheter 150 remains "preloaded" on a proximal portion of the guidewire 130. As such the placement process can be expedited and the number of inserted and removed from the insertion site can be reduced, mitigating the introduction of infection.

FIG. 6A shows a longitudinal cross-sectional side view of the needle 120 and splitter system 180 prior to removal of the needle 120. FIG. 6B shows a longitudinal cross-sectional plan view of the needle 120 and splitter system 180 prior to removal of the needle 120. FIG. 6C shows a longitudinal cross-sectional plan view of the needle 120 and splitter system 180 after removal of the needle 120.

Once the guidewire 130 has been advanced through the needle lumen 122 and into the vasculature 80, the needle 120 can be withdrawn proximally (FIG. 5D). To disengage the needle 120 from the guidewire 130, the needle 120 can be withdrawn over a splitter system 180 disposed within the needle housing 170. The splitter system 180 can include a splitter wedge ("wedge") 182 supported by the housing 170 and extending radially inward into the needle channel 172. In an embodiment, the wedge 182 can extend radially inward through a wall of the needle 120. In an embodiment, the splitter system 180 can include a first wedge and a second wedge, disposed opposite the first wedge across a central longitudinal axis of the needle 120. The wedge(s) 182 can be configured to split the needle 120 along a longitudinal axis and separate the needle 120 into a first portion 120A and a second portion 120B. In an embodiment, the wedge(s) 182 can be arranged along a transverse plane, a lateral plane, or along a plane extending at an angle relative thereto. In an embodiment, the wedge 182 can include a blade or similar sharpened edge, disposed at a distal end thereof. The wedge 182 can include a plastic, polymer, metal, alloy, hardened steel, composite, mineral, diamond cutting edge, or combinations thereof. In an embodiment, the wedge 182 can be disposed distally of one or both of the guidewire aperture 124 and guidewire channel 174 of the housing 170. In an embodiment, the wedge 182 can be disposed proximally of one or both of the guidewire aperture 124 and guidewire channel 174 of the housing 170.

In an embodiment, the needle 120 can include a tear line 126 extending longitudinally along the needle 120 and aligned with the wedge 182. The tear line 126 can include a perforation, laser cut line, groove, score line, or similar line of weakness configured to facilitate separation of the needle 120 therealong. It is important to note that the tear line 126 can also be configured to be fluid impermeable and can prevent any fluid passing therethrough prior to the needle 120 being split into two separate portions 120A, 120B. As such, the needle 120 can maintain the integrity of the needle lumen 122 and does not require any secondary sheath, or the like, disposed over the tear line 124 to mitigate fluids from leaking into or out of the needle lumen 122.

In an embodiment, the splitter system 180 can further include a valve 184. The valve 184 can extend annularly about the needle 120 and extend between an outer surface of the needle 120 and an inner surface of the needle channel 172 to maintain a fluid tight seal therebetween. In an embodiment, the valve 184 can extend longitudinally from a first point that is distal of one or both of the wedge 182 and the guidewire aperture 124, to a second point that is proximal of one or both of the wedge 182 and the guidewire aperture 124. In an embodiment, the splitter system 180 includes a first valve 184 disposed at the first point that is distal of one or both of the wedge 182 and the guidewire aperture 124, and a second valve 184 disposed at the second point that is proximal of one or both of the wedge 182 and the guidewire aperture 124.

In an embodiment, the splitter system 180 can further include a third valve 184 disposed within the guidewire channel 174 of the housing 170 and configured to mitigate fluid leakage therethrough. The third valve 184 can extend between an outer surface of the guidewire 130 and an inner wall of the guidewire channel 174 to provide a fluid tight seal therebetween. As such, the valve(s) 184 can prevent or mitigate a fluid from escaping from needle lumen, for example through one or both of the guidewire aperture 124 and the guidewire channel 174 of the housing 170. Optionally, when the syringe system 140 applies a vacuum to the needle lumen 122, the valve 184 can maintain the integrity of the vacuum within the needle lumen 122 to draw a fluid from a distal tip 128 and prevent a fluid flow from entering the needle lumen 122 through a proximal portion, for example, the guidewire aperture 124. As shown in FIG. 6C, as the needle 120 is withdrawn proximally over the splitter system 180, the wedge 182 can separate both the needle 120 and the valve 184 along a longitudinal axis. The guidewire 130 can then pass between the two portions of the needle 120 and the valve 184 to disengage the needle 120, splitter system 180 and housing 170 assembly.

In an embodiment, as shown in FIGS. 7A-10C, the catheter placement system 100 can further include a needle safety system 190. The needle safety system 190 can be configured to engage one or both of the first needle portion 120A and the second needle portion 120B, and encapsulate theses portions 120A, 120B, mitigating any damage to surrounding structures, causing trauma, or exposing a user to body fluids, as the needle 120 withdrawn proximally. For example, splitting the needle 120 longitudinally can create a sharpened edge along a longitudinal top edge or bottom edge of the first portion 120A or the second portion 120B. These sharpened edges can cause damage to surrounding structures of the system 100 or can cause injury to the user or patient, as the needle 120 is withdrawn proximally. Further, the needle 120 being withdrawn from the vasculature 80 may include body fluids, e.g. blood etc., disposed thereon. Encapsulation of the needle 120 by the needle safety system 190 can mitigate damage to surrounding structures, trauma to the user or patient, and exposure of these body fluids to the user.

Figure 7A:
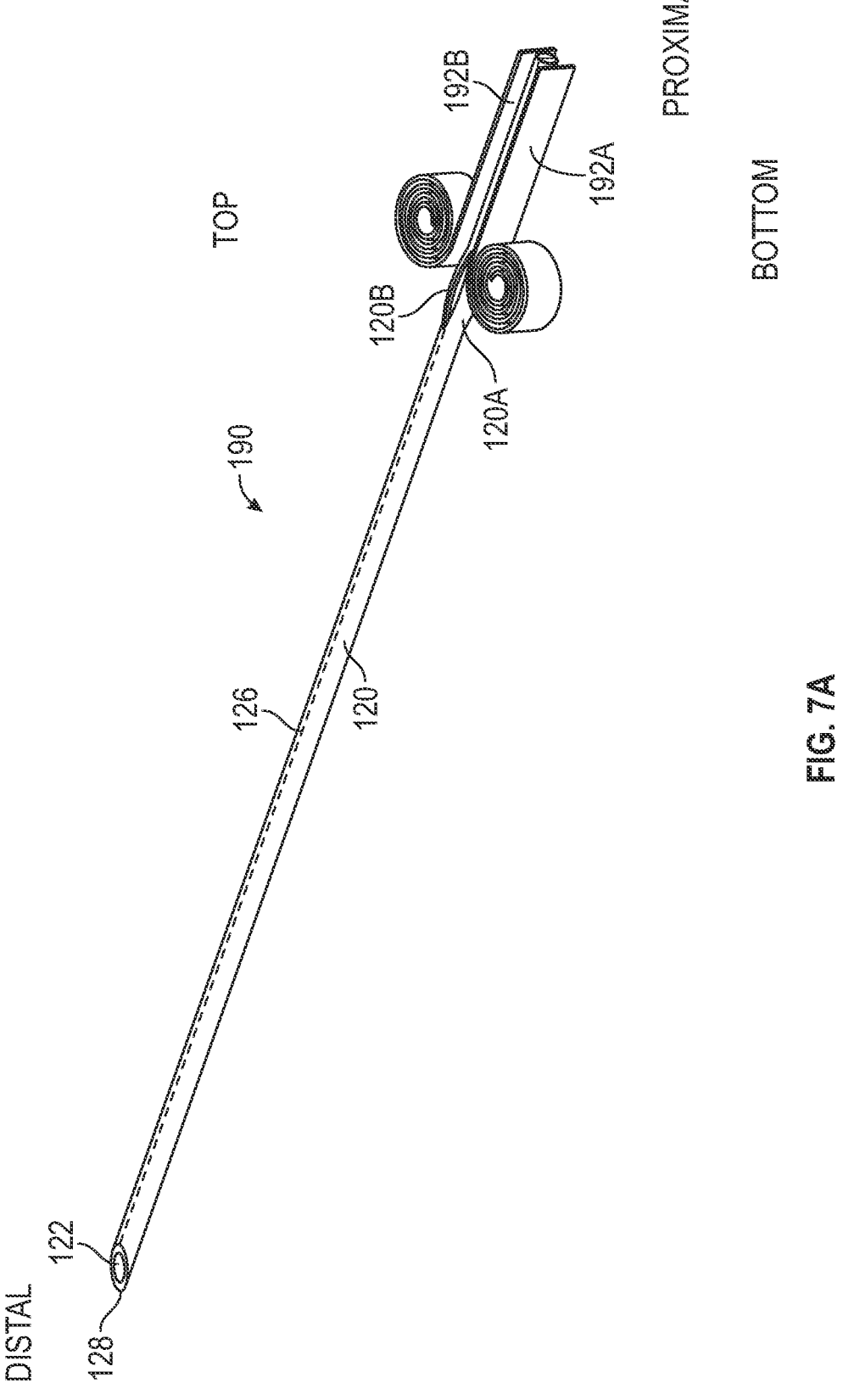
FIG. 7A shows a perspective view of a needle and needle safety system for a catheter placement system, in accordance with embodiments disclosed herein.
Figure 7B:
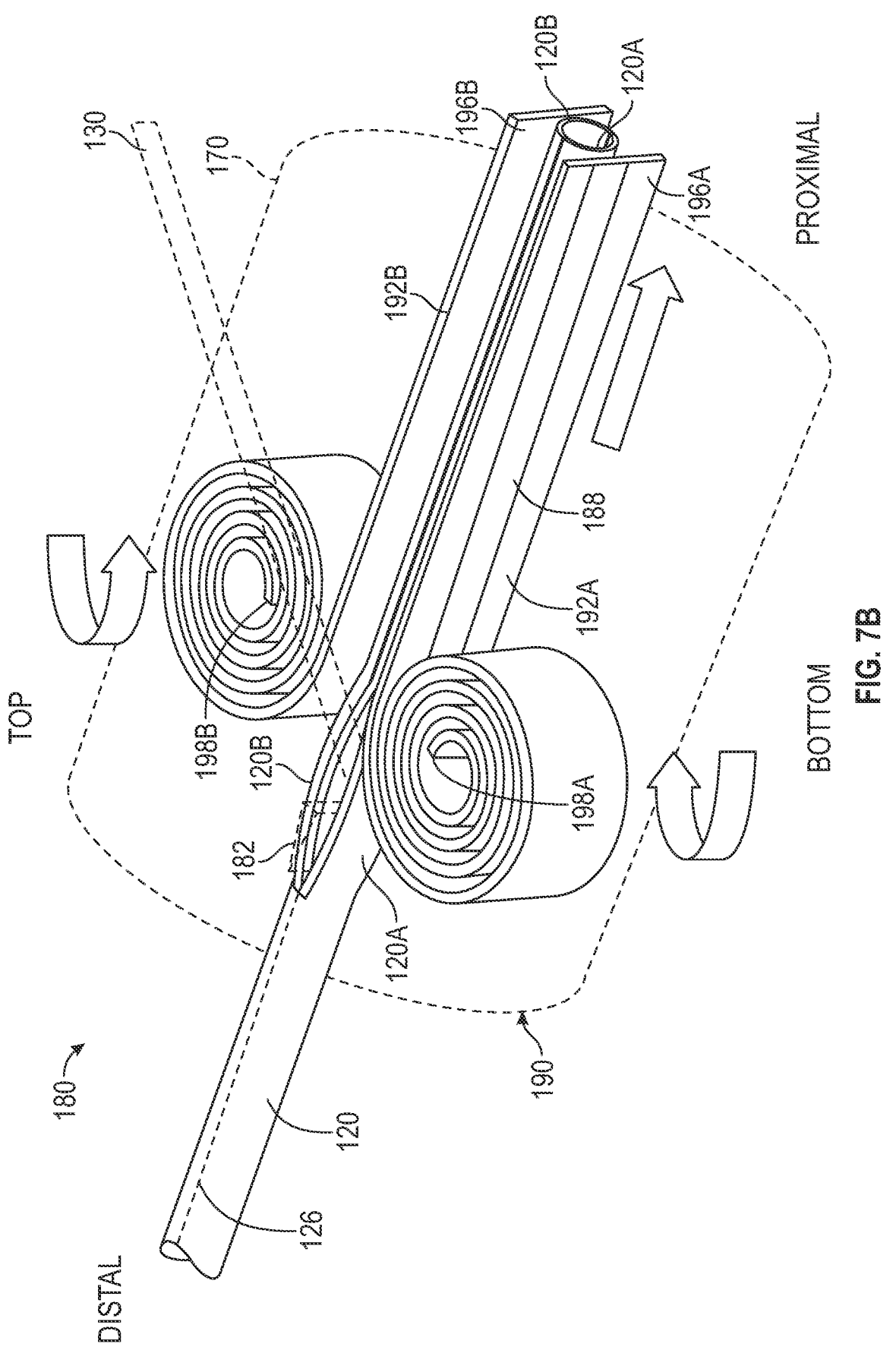
FIG. 7B shows close up detail of a needle safety system, in accordance with embodiments disclosed herein.
Figures 8A, 8B:
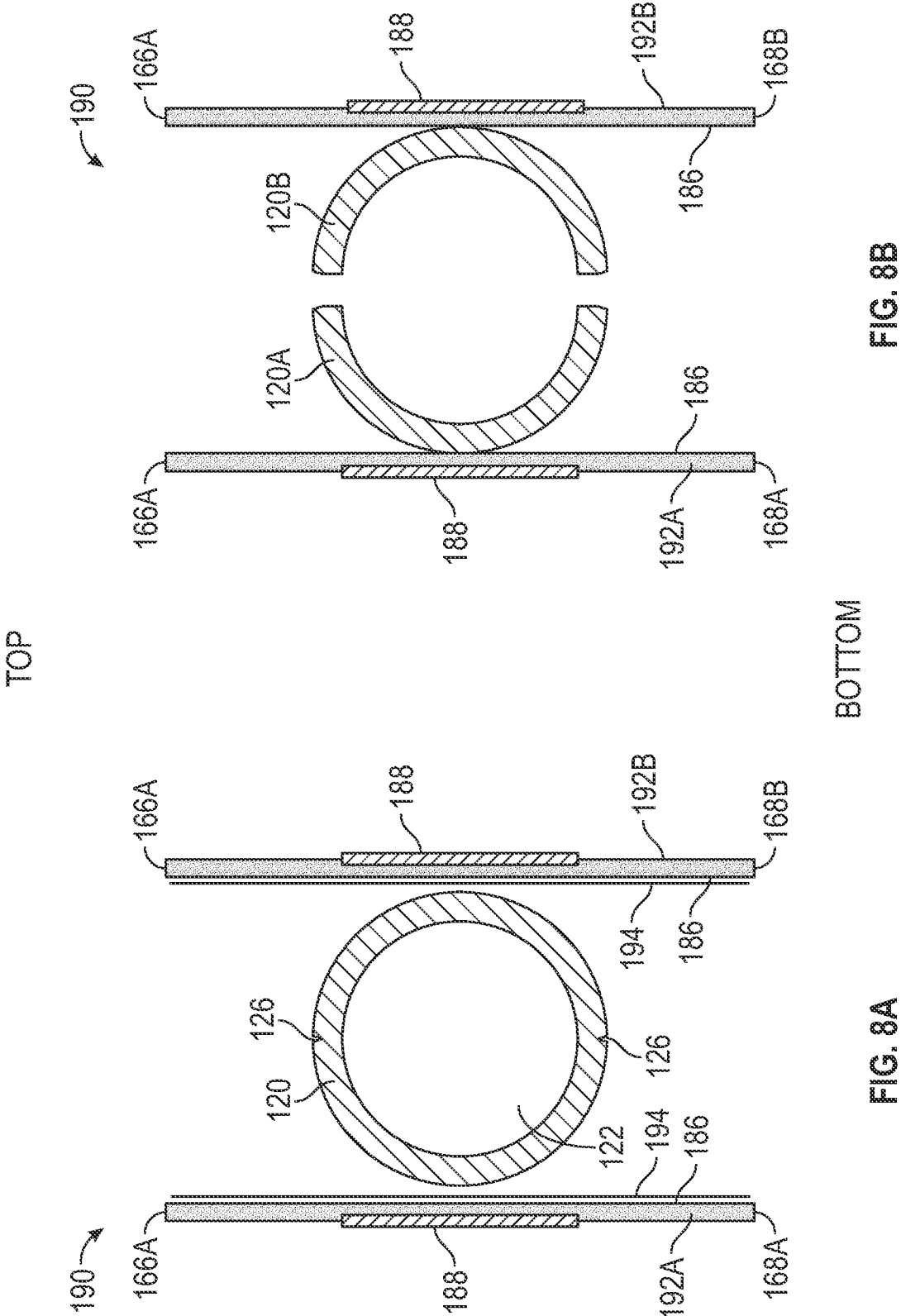

In an embodiment, the needle safety system 190 can include one or more tapes 192, for example a first tape 192A and a second tape 192B. The tape 192 can be formed of a first material and can include a flexible, puncture-resistant material such as a plastic, polymer, metal, alloy, composite, KEVLAR®, combinations thereof, or the like. In an embodiment, as shown in FIGS. 7B, 8A-8B, the tape 192 can include a reinforcement 188. In an embodiment, the reinforcement 188 can include a thickened portion of the first material of the tape 192. In an embodiment, the reinforcement 188 can include a second material, different from the first material, and can include more rigid, or more puncture-resistant mechanical properties. For example the reinforcement 188 can include, a metal, alloy, polymer, composite, KEVLAR®, combinations thereof, or the like. In an embodiment, the reinforcement 188 can be disposed on an outer surface, an inner surface, or disposed within a wall of the tape 192. In an embodiment, the reinforcement 188 can extend longitudinally along a length of the tape 192. Advantageously, the reinforcement 188 can mitigate sharpened edges of the needle portions 120A, 120B from penetrating the tape 192 and exposing the needle portions 120A, 120B risking damage, trauma, or exposure to the user, as described herein.

In an embodiment, the tape 192 can include an adhesive layer 186 disposed on a surface of the tape 192, e.g. one or both of an inner surface and an outer surface. The adhesive layer 186 can be configured to adhere the tape 192 to the needle 120, or a portion thereof. In an embodiment, the adhesive layer 186 can include a backing layer 194 configured to protect the adhesive layer prior to use, and prevent the adhesive layer 186 from adhering to a surface prematurely.

With continued reference to FIGS. 7A-7D, FIG. 7A shows the needle 120 and the needle safety system 190, with the housing 170 and needle splitter system 180 removed for ease of illustration. FIG. 7B shows close up detail of the needle 120 and needle safety system 190 with the housing 170, splitter system 180 and guidewire 130 shown in wire frame for ease of illustration. In an embodiment, the tape 192 can be disposed in a rolled configuration within the housing 170, however, other configurations of the tape 192, prior to deployment, are also contemplated. The tape 192 in the rolled configuration can be disposed proximally of the wedge 182. In an embodiment, a proximal end 196 of the tape 192 can be adhered to a proximal portion of the needle 120, for example a first proximal end 196A of the first tape 192A can be adhered to the first needle portion 120A, and a second proximal end 196B of the second tape 192B can be adhered to the second needle portion 120B.

Figures 7C, 7D, 8C:
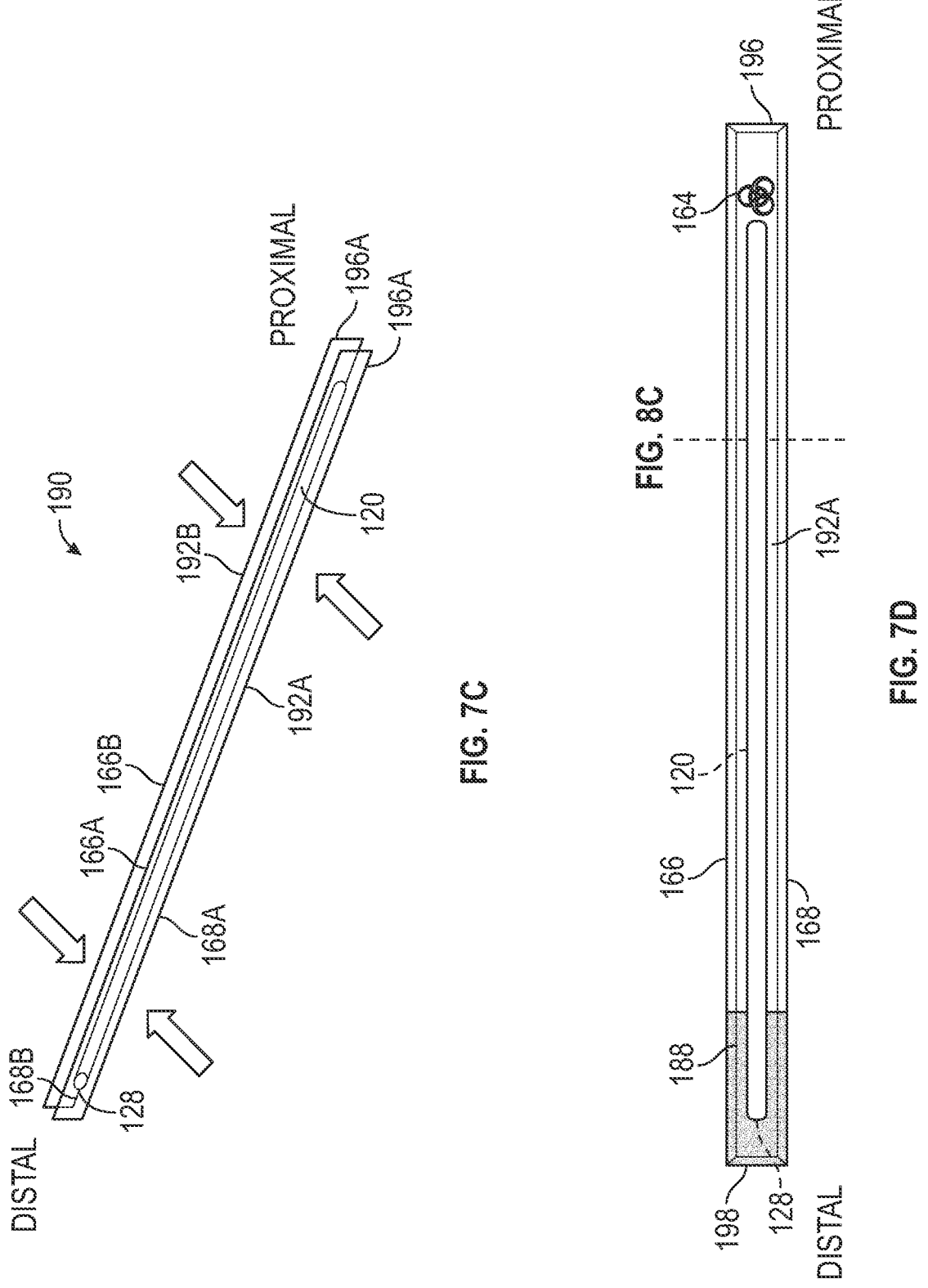
FIG. 7C shows a perspective view of a needle disposed between a first tape and a second tape of a needle safety system, in accordance with embodiments disclosed herein.
FIG. 7D shows a side view of a needle encapsulated by a needle safety system, in accordance with embodiments disclosed herein.
FIGS. 8A-8E show lateral cross-section views of exemplary methods of use for a needle and needle safety system, in accordance with embodiments disclosed herein.

In an embodiment, as shown in FIGS. 7C-7D, as the needle 120 is withdrawn proximally, the tapes 192A, 192B can transition from the rolled configuration to an unrolled configuration and adhere to the respective portions 120A, 120B of the needle, encasing the portions 120A, 120B and more specifically the sharpened edges, along an entire length of the needle 120.

FIG. 7C shows a perspective view of the needle 120 disposed between the tapes 192A, 192B, in the unrolled configuration. The tapes 192A, 192B can then adhere together to encapsulate the needle 120 therebetween. FIG. 7D shows a side view of the needle 120 encapsulated within tapes 192A, 192B adhered together. In an embodiment, a distal end 198 of the tape 192 can extend distally of the distal needle tip 128. As such, a distal portion of the first tape 192A adhered to a distal portion of the second tape 192B can mitigate the sharpened needle tip 128 from causing any accidental needle stick injuries. In an embodiment, a distal portion of the tape 192 can include a reinforcement 188, as described herein. The reinforcement 188 can create a hardened, or reinforced distal portion of the tapes 192A, 192B to encapsulate the sharpened distal needle tip 128 and mitigate accidental needle stick injuries. In an embodiment, an outer surface of one or both of the first tape 192A and the second tape 192B can include symbol 164 such as by way of non-limiting examples, an alphanumeric symbol, a Globally Harmonized System of Classification and Labeling ("GHS") symbol, a Hazard Communication Standard (HCS) symbol, a color, a texture, or similar visual or tactile indication that the tape 192 is engaged with a bio hazard, or a sharp object, and requires suitable disposal. Advantageously, the symbol 164 can mitigate mishandling of used needle 120. Further, pre-printing the symbol 164 and can reduce the workload to the user, mitigating human error in the handling of the used needle 120.

FIGS. 8A-8E show exemplary methods of encapsulating the needle 120 within the tapes 192A, 192B. FIGS. 8A-8E show lateral cross section views of the needle 120 and tapes 192A, 192B. FIG. 8A shows the needle 120 and the tapes 192A, 192B before the needle 120 is split by the splitter system 180. FIG. 8B shows the needle 120 having been split into a first portion 120A and a second portion 120B. With the backing layer(s) 194 removed, an adhesive surface 186 of the first tape 192A can adhere to an outer surface of the first needle portion 120A and an adhesive surface 186 of the second tape 192B can adhere to an outer surface of the second needle portion 120B. In an embodiment, the tape 192 can include a reinforcement 188 extending longitudinally, as described herein. To note, in splitting the needle 120 along tear lines 126, the longitudinal top edge and the longitudinal bottom edge of the first needle portion 120A and the second needle portion 120B can be sharpened and can cause damage or trauma. Encapsulating the top edge and the bottom edge of the first needle portion 120A and the second needle portion 120B can mitigate any damage or trauma.

FIG. 8C shows an embodiment of encapsulating the first portion 120A and the second portion 120B of the needle 120 where a top portion of the first tape 192A adheres to a top portion of the second tape 192B, and a bottom portion of the first tape 192A adheres to a bottom portion of the second tape 192B, encapsulating the needle 120 therebetween. In an embodiment, as shown in FIG. 7B, the encapsulation of the needle portions 120A, 120B can occur within the housing 170 and proximal of the guidewire 130 disengaging the needle 120. As such, the needle 120 can be encapsulated prior to exiting the housing 170, mitigating any accidental damage or trauma, or accidental exposure of the user to body fluids.

Figures 8C, 8D:
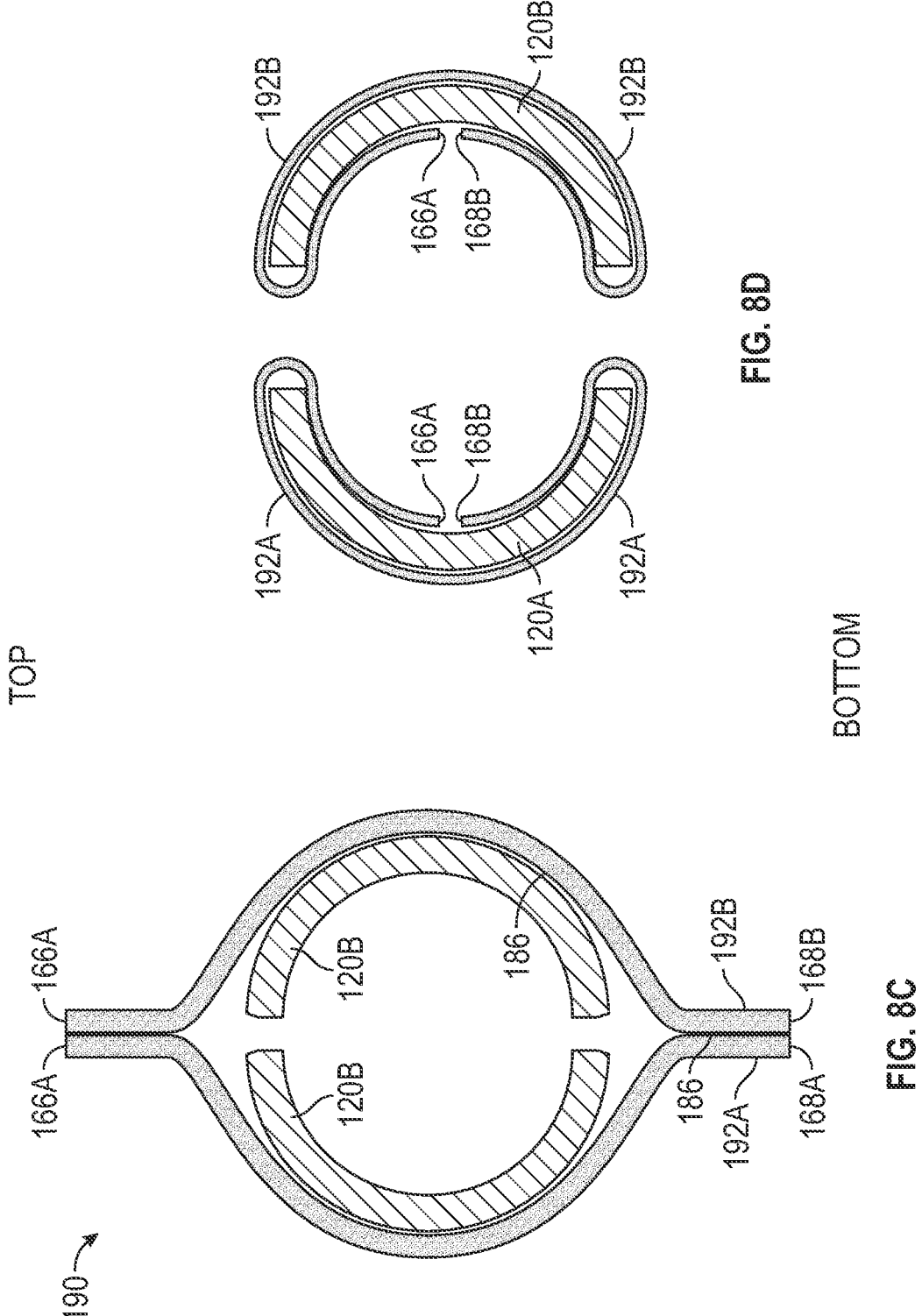
Figure 8E:
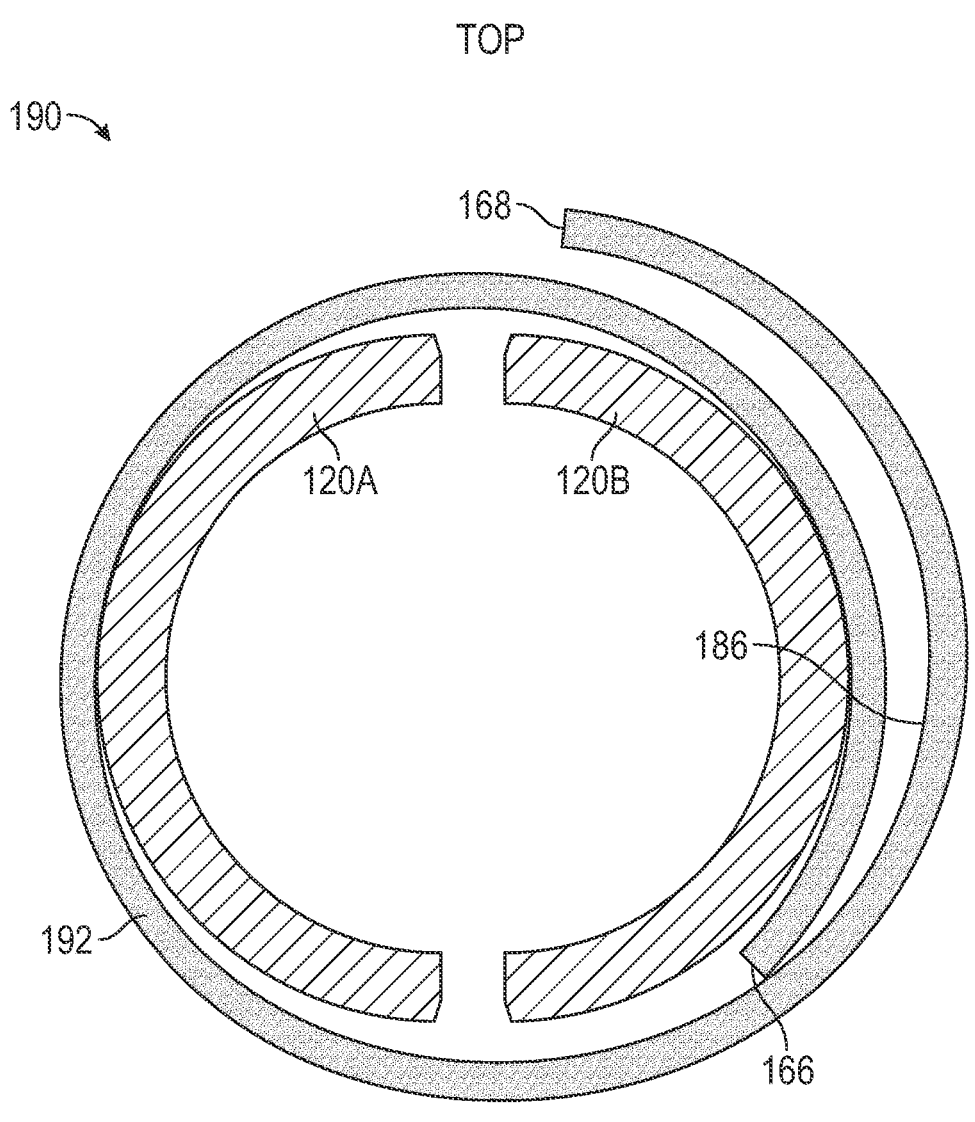

In an embodiment, as shown in FIG. 8D, a top edge 166 and a bottom edge 168 of the tape 192 can fold over a top edge and a bottom edge of a respective needle portion and can adhere to an inner surface thereof. As such, the first tape 192A can encapsulate a first needle portion 120A, and the second tape 192B can encapsulate a second needle portion 120B. In an embodiment, as shown in FIG. 8E, the needle safety system 190 can include a single tape 192, as described herein, having a width sufficient to encapsulate one or both of the first needle portion 120A and the second needle portion 120B. For example, a width of the tape 192 can extend between the top edge 166 and the bottom edge 168 substantially perpendicular to a longitudinal axis. As shown in FIG. 8E, the width of the tape 192 can be configured to encircle the needle 120, or a portion thereof, and a bottom edge 168 can overlap a top edge 166. In an embodiment, a top edge 166 can overlap a bottom edge 168, encapsulating the needle 120, or a portion thereof. Advantageously, these methods of encapsulating the needle portion 120A, 120B can mitigate contact between the sharpened edges of the needle and the tape 192. As such, this can mitigate the sharpened edges from rubbing against, and penetrating the tape 192, which might expose the needle 120 to the user.

Figure 9A:
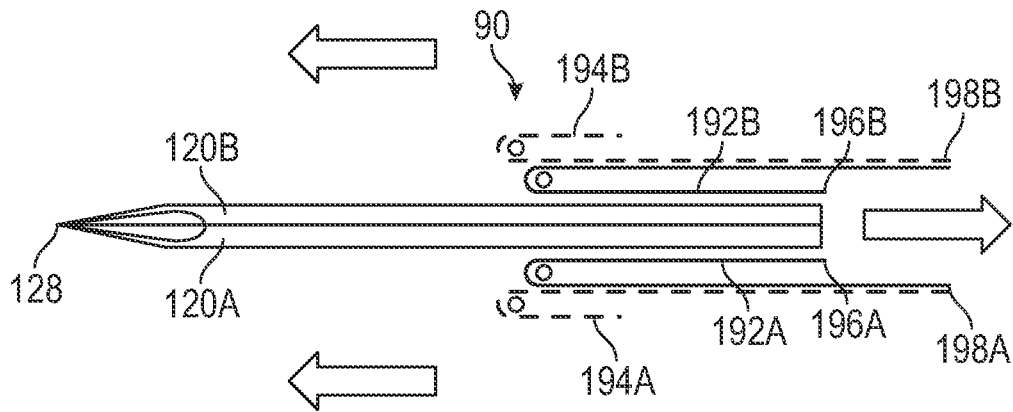
FIGS. 9A-9B show plan views of an exemplary method of use for a needle and needle safety system, in accordance with embodiments disclosed herein.
Figure 9B:
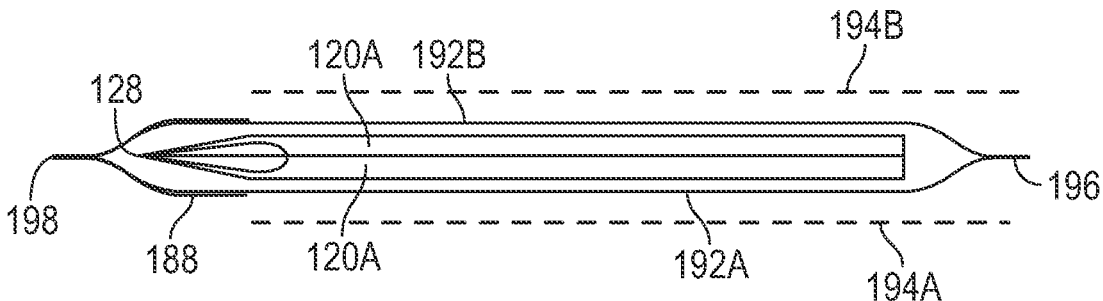

In an embodiment, as shown in FIGS. 9A-9B the needle safety system 190 can include one or more gears, spindles, or the like configured to peel the backing layer 194 off of the tape 192 and adhere the tape 192 to the needle 120, or a portion thereof, as the needle 120 is withdrawn proximally, encapsulating the needle 120 as described herein. As shown in FIGS. 9A-9B, the tape 192 can include an adhesive surface 186 disposed on an inner surface and can be adhered to an outer surface of the needle 120, encapsulating the needle 120 as described herein.

Figure 10A:
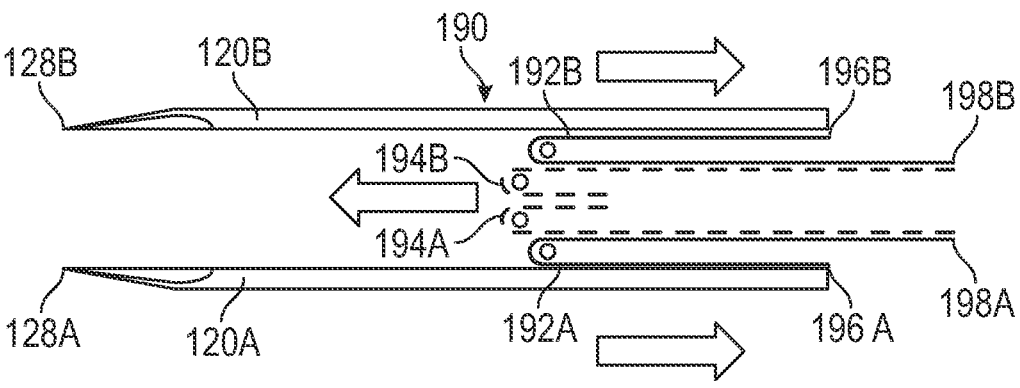
FIGS. 10A-10B show plan views of an exemplary method of use for a needle and needle safety system, in accordance with embodiments disclosed herein.
Figure 10B:
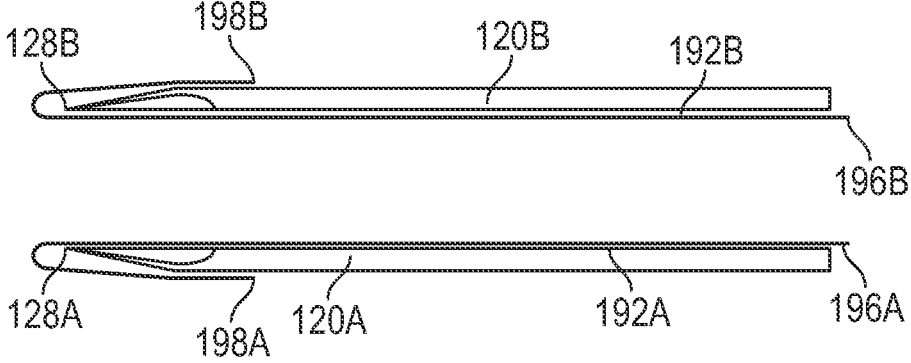
Figure 10C:
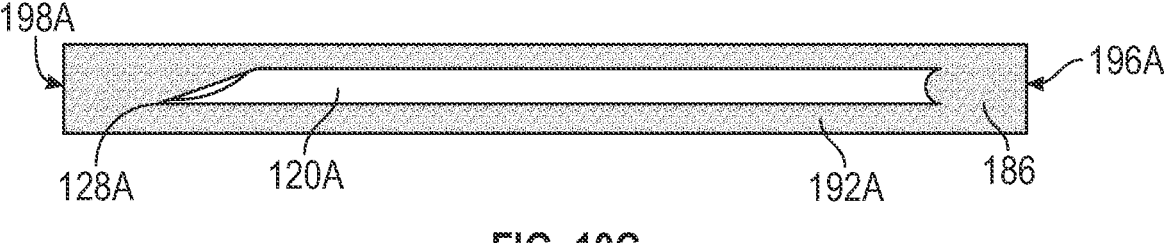
FIG. 10C shows a side view of a needle and needle safety system, in accordance with embodiments disclosed herein.

In an embodiment, as shown in FIGS. 10A-10C the needle safety system 190 can be configured to remove the backing layer 194 and adhere the tape 192 to an inner surface of the needle portions 120A, 120B. The tapes 192A, 192B can include an adhesive layer disposed on an outer surface. FIGS. 10A-10B show a plan view of the needle 120 and needle safety system 190. FIG. 10C shows a side view of a first needle portion 120A adhered to a first tape 192A. In an embodiment, as shown in FIG. 10B, a distal end 198 of the tape 192 can be folded outwards and over the distal tip 128 of the needle 120 to mitigate accidental needle stick injuries. For example, a first distal end 198A of the first tape 192A can be folded outwards and back on to the first tape 192A to encapsulate the sharpened distal tip 128A of the first portion 120A of the needle 120. Similarly, a second distal end 198B of the second tape 192B can be folded outwards and back on to the second tape 192B to encapsulate the sharpened distal tip 128B of the second portion 120B of the needle 120. In an embodiment, a top edge 166 and a bottom edge 168 of the tape 192 can fold outwards and adhere to an outer surface, or can overlap, to encapsulate the needle portions 120A, 120B, as described herein.

Advantageously, these methods of encapsulating the needle portion 120A, 120B can mitigate contact between the sharpened edges of the needle and the tape 192. As such, this can mitigate the sharpened edges from rubbing against, or penetrating, the tape 192, which might expose the needle 120 to the user.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A catheter placement system, comprising:
a needle defining a needle lumen;
a guidewire extending through a portion of the needle lumen;
a housing defining a needle channel and having a portion of the needle slidably engaged therewith;
a splitter system disposed within the housing and configured to split the needle longitudinally as the needle is withdrawn proximally through the needle channel; and
a needle safety system having one or both of a first tape and a second tape configured to encapsulate one or both of a first portion and a second portion of the needle after the needle has been split by the splitter system.

2. The catheter placement system according to claim 1, wherein the needle is supported at a proximal end by one or both of a needle hub and a syringe system, the syringe system configured to draw a fluid flow proximally through the needle lumen.

3. The catheter placement system according to claim 1, wherein the housing further includes a guidewire channel communicating with the needle channel, the guidewire channel aligned with an aperture disposed in a wall of the needle and communicating with the needle lumen, a portion of the guidewire extending through the guidewire channel, through the aperture and into the needle lumen.

4. The catheter placement system according to claim 3, wherein the splitter system includes a wedge disposed distally of the aperture and configured to split the needle along a longitudinal axis.

5. The catheter placement system according to claim 1, wherein the needle further includes a tear line extending longitudinally and aligned with the splitter system, the tear line configured to facilitate separation of the needle therealong.

6. The catheter placement system according to claim 1, wherein the splitter system further includes a valve extending between an outer surface of the needle and an inner surface of the needle channel and configured to mitigate fluid leakage to or from the needle lumen, the splitter system configured to split the valve as the needle is withdrawn proximally.

7. The catheter placement system according to claim 1, wherein one or both of the first tape and the second tape are disposed within the housing in a rolled configuration and are configured to transition to an unrolled configuration as the needle is withdrawn proximally from the housing.

8. The catheter placement system according to claim 1, wherein a top edge of the first tape is configured to adhere to a top edge of the second tape, and a bottom edge of the first tape is configured to adhere to a bottom edge of the second tape to encapsulate the first portion and the second portion of the needle therebetween.

9. The catheter placement system according to claim 7, wherein the first tape in the unrolled configuration is designed to encapsulate the first portion of the needle, and the second tape in the unrolled configuration is designed to encapsulate the second portion of the needle.

10. The catheter placement system according to claim 1, wherein a top edge of the first tape is configured to overlap a bottom edge of the first tape to encapsulate one or both of the first portion and the second portion of the needle.

11. The catheter placement system according to claim 1, wherein the first tape is adhered to a first inner surface of the first portion of the needle, a distal end of the first tape configured to fold outwards and adhere to a first outer surface of the first portion, and wherein the second tape is adhered to a second inner surface of the second portion of the needle, the distal end of the first tape configured to fold outwards and adhere to a second outer surface of the second portion.

12. The catheter placement system according to claim 1, wherein one or both of the first tape and the second tape include a first material, the first material including one or more of a plastic, a polymer, a metal, an alloy, a composite, or a puncture-resistant material.

13. The catheter placement system according to claim 1, wherein one or both of the first tape and the second tape include a reinforcement portion.

14. The catheter placement system according to claim 13, wherein the reinforcement portion includes one of a thickened portion or a second material different from the first material, the second material including one of a plastic, polymer, metal, alloy, composite, or a puncture-resistant material.

15. The catheter placement system according to claim 1, further including a catheter disposed on a proximal portion of the guidewire.

16. The catheter placement system according to claim 15, wherein the catheter includes a first section disposed distally and defining a first diameter, a second section disposed proximally and defining a second diameter, larger than the first diameter, and a transition section extending therebetween.

17. The catheter placement system according to claim 16, wherein the first section defines a single lumen and the second section defines two or more lumen.

18. A method of encapsulating a needle of a catheter placement system, comprising:
accessing a vasculature of a patient with the needle;
advancing a portion of a guidewire through a lumen of the needle;
withdrawing the needle proximally through a channel of a housing;
splitting the needle longitudinally into a first needle half and a second needle half;
disengaging the guidewire from the needle by passing the portion of the guidewire longitudinally between the first needle half and the second needle half; and
engaging one or both of the first needle half and the second needle half with one or both of a first adhesive tape and a second adhesive tape.

19. The method according to claim 18, wherein the needle further includes a tear line extending longitudinally and configured to facilitate separating the needle longitudinally into the first needle half and the second needle half.

20. The method according to claim 18, further including advancing the portion of the guidewire through an aperture extending through a side wall of the needle and communicating with the lumen of the needle.

21. The method according to claim 18, further including withdrawing the needle over a splitter wedge to split the needle into the first needle half and the second needle half.

22. The method according to claim 18, further including adhering a first top edge of the first adhesive tape to a second top edge of the second adhesive tape, and adhering a first bottom edge of the first adhesive tape to a second bottom edge of the second adhesive tape to encapsulate the first needle half and the second needle half between the first adhesive tape and the second adhesive tape.

23. The method according to claim 18, further including adhering the first adhesive tape to the first needle half, a top edge of the first adhesive tape extending over a top edge of the first needle half to adhere to an inner surface thereof, and a bottom edge of the first adhesive tape extending over a bottom edge of the first needle half to adhere to an inner surface thereof.

24. The method according to claim 23, further includes adhering the second adhesive tape to the second needle half, a top edge of the second adhesive tape extending over a top edge of the second needle half to adhere to an inner surface thereof, and a bottom edge of the second adhesive tape extending over a bottom edge of the second needle half to adhere to an inner surface thereof.

25. The method according to claim 18, further including adhering the first adhesive tape to one or both of the first needle half and the second needle half, a top edge of the first adhesive tape overlapping a bottom edge of the first adhesive tape.

26. The method according to claim 18, further including adhering the first adhesive tape to a first inner surface of the first needle half, and folding a distal portion of the first adhesive tape outwards to engage a first outer surface of the first needle half, and adhering the second adhesive tape to a second inner surface of the second needle half, and folding a distal portion of the second adhesive tape outwards to engage a second outer surface of the second needle half.

27. The method according to claim 18, wherein one or both of the first adhesive tape and the second adhesive tape include a first material, the first material including one or more of a plastic, a polymer, a metal, an alloy, a composite, or a puncture-resistant material.

28. The method according to claim 27, wherein one or both of the first adhesive tape and the second adhesive tape include a reinforcement portion having one of a thickened portion or a second material different from the first material, the second material including one of the plastic, the polymer, the metal, the alloy, the composite, or the puncture-resistant material.

* * * * *